United States Patent
Gaan et al.

(10) Patent No.: US 9,650,497 B2
(45) Date of Patent: May 16, 2017

(54) PHOSPHONAMIDATES-SYNTHESIS AND FLAME RETARDANT APPLICATIONS

(75) Inventors: Sabyasachi Gaan, St. Gallen (CH); Matthias Neisius, St. Gallen (CH); Primo Mercoli, Sevelen (CH); Shuyu Liang, St. Gallen (CH); Henri Mispreuve, Wangen (CH); Reinold Näscher, Gamprin-Bendern (LI)

(73) Assignees: EMPA EIDGENOSSISCHE MATERIALPRUFUNGS- UND FORSCHUNGSANSTALT, Dubendorf (CH); FRITZ NAUER AG, Wolfhausen (CH)

( * ) Notice: Subject to any disclaimer, the term of this patent is extended or adjusted under 35 U.S.C. 154(b) by 295 days.

(21) Appl. No.: 14/237,284

(22) PCT Filed: Aug. 6, 2012

(86) PCT No.: PCT/EP2012/003354
§ 371 (c)(1),
(2), (4) Date: May 20, 2014

(87) PCT Pub. No.: WO2013/020696
PCT Pub. Date: Feb. 14, 2013

(65) Prior Publication Data
US 2014/0343183 A1 Nov. 20, 2014

(30) Foreign Application Priority Data
Aug. 8, 2011 (EP) .................................... 11176861

(51) Int. Cl.
| | | |
|---|---|---|
| *C08K 5/5399* | (2006.01) | |
| *C07F 9/6571* | (2006.01) | |
| *C09K 21/12* | (2006.01) | |
| *C08J 9/00* | (2006.01) | |
| *C08K 5/544* | (2006.01) | |

(52) U.S. Cl.
CPC ...... *C08K 5/5399* (2013.01); *C07F 9/657181* (2013.01); *C08J 9/0038* (2013.01); *C08K 5/544* (2013.01); *C09K 21/12* (2013.01); *C08J 2375/04* (2013.01)

(58) Field of Classification Search
CPC ...... C08K 5/5399; C08K 5/544; C09K 21/12; C08J 9/0038; C08J 2375/04; C07F 9/657181
See application file for complete search history.

(56) References Cited

U.S. PATENT DOCUMENTS

| | | | |
|---|---|---|---|
| 8,227,138 B2* | 7/2012 | Choi ................. | C07F 9/657172 429/491 |
| 2006/0194045 A1* | 8/2006 | Masuda .................... | D01F 1/07 428/364 |
| 2009/0048377 A1* | 2/2009 | Kanno ................. | C08K 5/0066 524/117 |
| 2011/0034717 A1* | 2/2011 | Lu ..................... | C07F 9/657172 558/82 |
| 2011/0266507 A1* | 11/2011 | Fuchs .................. | C07F 9/3834 252/609 |
| 2011/0288206 A1* | 11/2011 | Fuchs ................. | C07D 251/54 523/451 |
| 2012/0157589 A1* | 6/2012 | Roth .................. | C08K 5/34928 524/101 |
| 2015/0051327 A1 | 2/2015 | Kobayashi et al. | |

FOREIGN PATENT DOCUMENTS

| | | |
|---|---|---|
| CN | 101184810 A | 5/2008 |
| WO | WO 03/016373 | 2/2003 |
| WO | 2008088487 A2 | 7/2008 |

OTHER PUBLICATIONS

Bykov, Yana, et al., Synthesis of New Dibenzo [c.e] [1,2] oxaphosphorine 2-oxide Containing Diols Based on Diethanolamine, Heteratom Chemistry, vol. 23, Nov. 2, 2012, pp. 146-153.
Kerenyi, Andrea, et al., Synthesis and complexation of novel dibenzo [c.e] [1,2] oxaphosphorine-based P-ligands, Transition Met Chem (200) 33:459-465.

* cited by examiner

*Primary Examiner* — John Cooney
(74) *Attorney, Agent, or Firm* — Notaro, Michalos & Zaccaria P.C.

(57) ABSTRACT

A group of novel compounds containing one or more amino substituted DOPO (9,10-dihydro-9-oxa-phosphaphenthren-10-oxide) moieties. The compounds were found to have good flame retardant properties and also good thermal stability, which makes them particularly suitable as flame retardant additives for various thermoplastic polymers. In particular, they can be incorporated in a polyurethane foam.

20 Claims, 4 Drawing Sheets

PHOSPHONAMIDATES-SYNTHESIS AND FLAME RETARDANT APPLICATIONS

TECHNICAL FIELD OF THE INVENTION

The present invention relates to novel phosphonamidate compounds and to their use as flame retardant substances.

BACKGROUND OF THE INVENTION

These days polymers based on various organic monomers are present almost everywhere around us. They are equally used for exterior as well as interior purposes. For that reason it is very important to make most of these polymers flame retardant to minimize the risk of fires. In the past most common flame retardants were halogenated organic compounds which showed a very high efficiency in flame retardation of polymers. These halogenated compounds act by gas-phase mechanism, which means that in case of fire they decompose and easily release halogen-radicals. These halogen radicals act as a scavenger to trap reactive H*- and OH*-radicals so that there is no heat flow to sustain the flame. Nowadays some of these halogen based flame retardants have been banned because they are environmentally not very benign. Hence there is more than ever a need of novel flame retardants that are able to replace and act like halogenated ones.[1] DOPO (9,10-dihydro-9-oxa-phosphaphenanthrene-10-oxide)[2] and some derivatives thereof have drawn much attention in the last decade due to their flame retardant properties.[3] It is mainly accepted and investigated in detail that these compounds predominantly act by a gas phase-mechanism.[4]

Scheme 1: DOPO and its derivatives

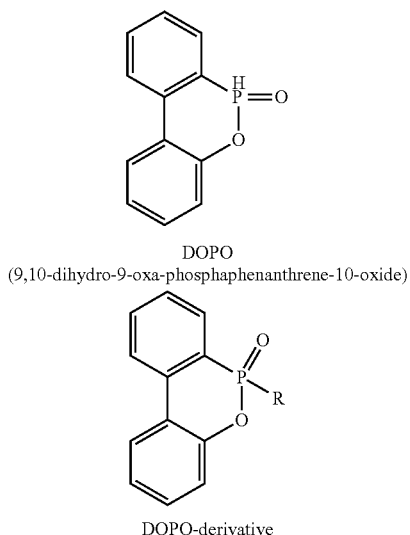

DOPO
(9,10-dihydro-9-oxa-phosphaphenanthrene-10-oxide)

DOPO-derivative

During combustion they decompose and release low molecular weight phosphorus-containing fragments that are able to scavenge H*- and OH*-radicals.[4a,5]

In the literature there are a lot of reports dealing with the synthesis and flame retardant application of alkyl DOPO-derivatives.[3,6]

Apart from this, one can also find several reports dealing with the synthesis and application as flame retardant of alkoxy DOPO-derivatives. In contrast to the derivatives mentioned above one could find some publications dealing with amino DOPO-derivatives.[7,8] To the best of our knowledge there are only few reports which describe the synthesis and characterization of amino-DOPO derivatives.[7h-k] Again the synthesis proceeds via a two-step reaction sequence as mentioned before.[8]

Scheme 2: Preparation of amino-DOPO derivatives via a two-step reaction sequence[8]

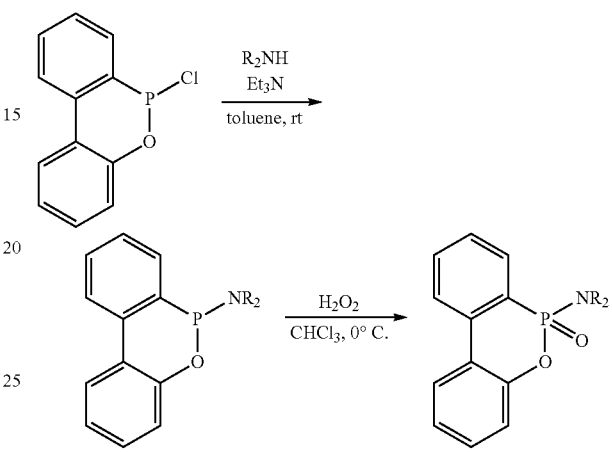

Additionally one can also find a few amino-thio-DOPO derivatives in literature.[9] Although phosphinate derivatives of DOPO are commonly known as flame retardants for various polymeric systems, the amino derivatives of DOPO are not well studied as flame retardants. It is known that organophosphorus compounds containing a P—N bond i.e. phosphoramidates exhibit superior flame retardant properties for example on cellulose.[10] Hence it would be interesting to develop amino derivatives of DOPO and evaluate them, for their FR efficacy. There are a few patent documents mentioning flame retardant application of amino-DOPO derivatives on various polymeric resin compositions[7]. But the derivatives reported in these patent documents have not been characterized by appropriate analytical methods. Some alkylamino-DOPO derivatives have also been mentioned in EP 1889878 A1 as possible flame retardant structures. However, in said patent document there is no report on such structures having been prepared nor is any method of their preparation elaborated.[11] Furthermore there are amino derivatives of DOPO which have been reported as component in organic light emitting diodes (OLEDs), batteries and azo-dyes.[8]

Scheme 3: Amino-DOPO derivatives previously described in the Literature

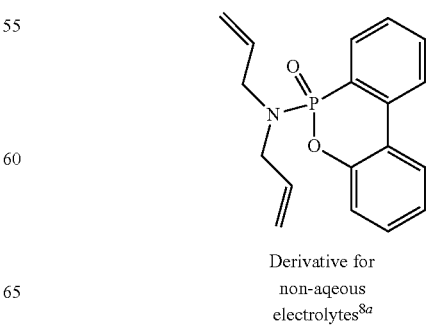

Derivative for
non-aqeous
electrolytes[8a]

-continued

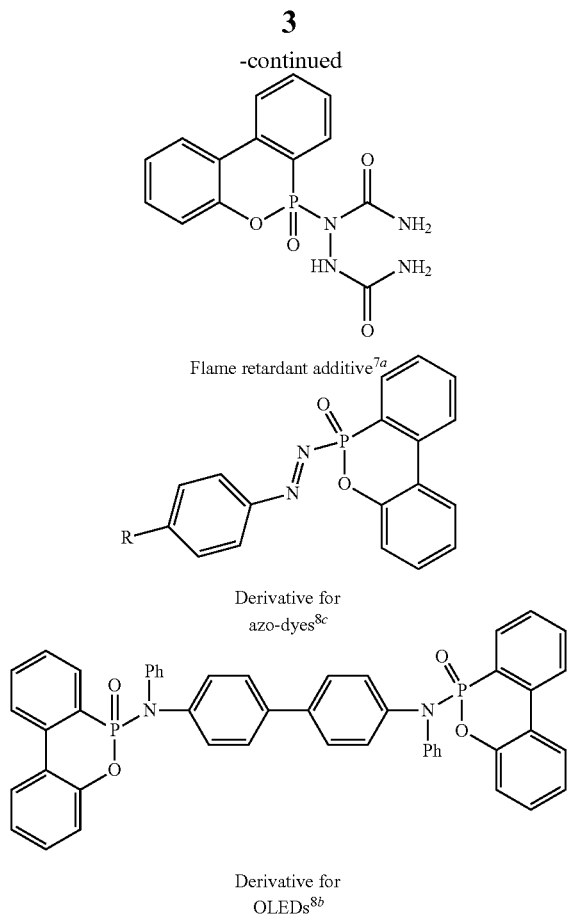

Flame retardant additive[7a]

Derivative for azo-dyes[8c]

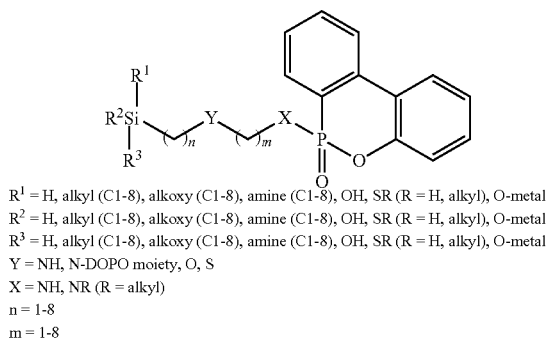

Derivative for OLEDs[8b]

SUMMARY OF THE INVENTION

According to one aspect of the invention, there is provided a group of novel phosphonamidate compounds, which are particularly contemplated for their flame retardant properties in combination with an improved thermal stability and concomitant processability at elevated temperatures such as in a thermoplastic process. The phosphonamidate compounds are selected from the group consisting of:
AA-DOPO;
BHEA-DOPO;
PB-DOPO;
PDAB-DOPO;
a compound according to Formula (I)

(I)

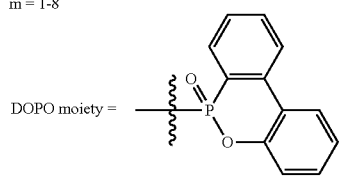

$R^1$ = H, alkyl (C1-8), alkoxy (C1-8), amine (C1-8), OH, SR (R = H, alkyl), O-metal
$R^2$ = H, alkyl (C1-8), alkoxy (C1-8), amine (C1-8), OH, SR (R = H, alkyl), O-metal
$R^3$ = H, alkyl (C1-8), alkoxy (C1-8), amine (C1-8), OH, SR (R = H, alkyl), O-metal
Y = NH, N-DOPO moiety, O, S
X = NH, NR (R = alkyl)
n = 1-8
m = 1-8

DOPO moiety = particularly:
TESPA-DOPO, or
TMSPA-DOPO;
a compound according to Formula (II)

(II)

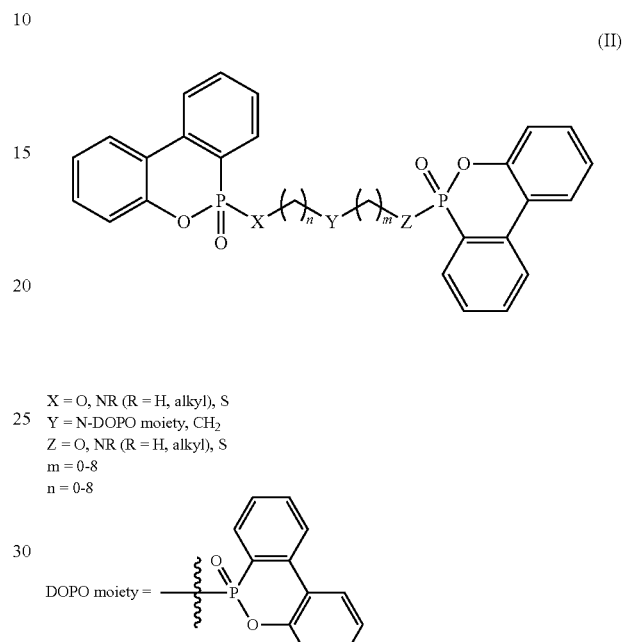

X = O, NR (R = H, alkyl), S
Y = N-DOPO moiety, CH$_2$
Z = O, NR (R = H, alkyl), S
m = 0-8
n = 0-8

DOPO moiety = particularly:
EAB-DOPO,
DEA-DDOPO, or
DEA-TDOPO;
a compound according to formula (III)

(III)

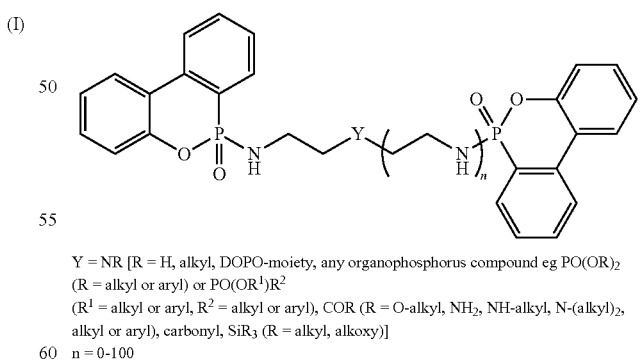

Y = NR [R = H, alkyl, DOPO-moiety, any organophosphorus compound eg PO(OR)$_2$
(R = alkyl or aryl) or PO(OR$^1$)R$^2$
(R$^1$ = alkyl or aryl, R$^2$ = alkyl or aryl), COR (R = O-alkyl, NH$_2$, NH-alkyl, N-(alkyl)$_2$,
alkyl or aryl), carbonyl, SiR$_3$ (R = alkyl, alkoxy)]
n = 0-100 and mixtures thereof,
particularly:
EDAB-DOPO, or
TDETA-DOPO, a compound according to formula (IV)

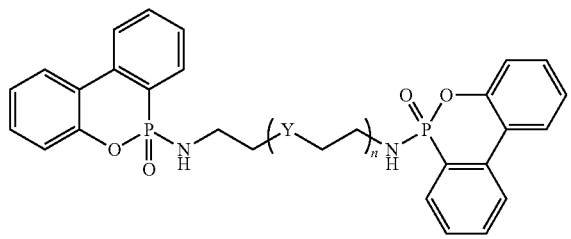

Y = NR [R = H, alkyl, DOPO-moiety, any organophosphorus compound eg PO(OR)$_2$ (R = alkyl or aryl) or PO(OR$^1$)R$^2$ (R$^1$ = alkyl or aryl, R$^2$ = alkyl or aryl), COR (R = O-alkyl, NH$_2$, NH-alkyl, N-(alkyl)$_2$, alkyl or aryl), carbonyl, SiR$_3$ (R = alkyl, alkoxy)]
n = 0-100 and mixtures thereof,
particularly:
TEPA-PDOPO.

The above mentioned acronyms shall have the meaning as unambiguously defined in the Examples given further below. Preferably, Y as referred to in formulae III and IV is NR wherein R=H, alkyl, DOPO-moiety, PO(OR)$_2$ (R=alkyl or aryl), PO(OR$^1$)R$^2$ (R$^1$=alkyl or aryl, R$^2$=alkyl or aryl), COR(R=O-alkyl, NH$_2$, NH-alkyl, N-(alkyl)$_2$, alkyl or aryl), SiR$_3$ (R=alkyl, alkoxy). More preferably, for COR within the definition of Y, R=alkyl or aryl.

The compounds of Formula (I) represent a wide variety of functionalized silane or siloxane derivatives.

The compounds of Formula (II) represent a wide variety of "multi-DOPO derivatives", i.e. of compounds containing at least two DOPO entities.

The compounds of Formula (III) and Formula (IV) represent a further variety of "multi-DOPO derivatives" which are based on a polyethyleneamine backbone to which there are attached at least two DOPO entities. The backbone can comprise up to 100 amine units. The compounds of Formula III can be obtained by reacting a polyethyleneamine template with an excess of DOPO, which result in a mixture of poly-DOPO amino derivatives. Such a mixture can generally be considered as an oligomeric mixture that may not be subject to the REACH regulations.

It is envisaged that in certain situations AA-DOPO, BHEA-DOPO and/or PDAB-DOPO may desirably be excluded from the group of suitable phosphonamidate compounds. They may be excluded individually, or in any permutation.

According to another aspect of the invention, there is provided a method of improving flame resistance of a polymeric material, comprising the step of adding a first amount of a phosphonamidate according to the present invention, or of a mixture thereof, as a flame retardant substance to a second amount of the polymeric material.

According to a further aspect of the invention, there is provided a polymeric material with improved flame resistance, comprising a flexible polyurethane foam containing an amount of about 1% to about 30%, preferably about 3% to about 25%, particularly about 5%, by weight per 100 parts of polyol of a flame retardant additive selected from a phosphonamidate of the invention, preferably from the group consisting of
EDAB-DOPO,
TEPA-PDOPO,
a compound of formula (IV) wherein n=2-10, preferably 3-10,
BHEA-DOPO,
DEA-DDOPO, And
mixtures thereof.

According to a yet further aspect of the invention, there is provided a polymeric material with improved flame resistance, comprising a rigid polyurethane foam containing an amount of about 1% to about 30% by weight, preferably about 1% to about 25%, particularly about 3%, by weight per 100 parts of polyol of a flame retardant additive selected from a phosphonamidate of the invention, preferably the group consisting of
EDAB-DOPO,
TEPA-PDOPO
a compound of formula (IV) wherein n=2-10, preferably 3-10,
BHEA-DOPO,
DEA-DDOPO,
mixtures thereof,
and optionally also comprising a synergist for example an efficient intumescent char former such as expandable graphite and/or an efficient carbonaceous char former such as pentaerythritol.

Further aspects of the invention provide methods of making phosphonamidate compounds using a single reaction step. Specifically there are provided methods of making a phosphonamidate comprising the steps: of dissolving DOPO and an amine in a solvent to form a mixture; optionally cooling the mixture to below about 20° C., 15° C., or 10° C. adding tetrachloromethane or trichloroisocyanuric acid to the mixture at a rate (i) such that the reaction temperature does not exceed about 30° C., or if the mixture was cooled, (ii) such that the reaction temperature does not exceed about 20°, 15° C. or 10° C.; allowing the mixture to return to about 25° C.; and stirring the mixture. Preferably the solvent is dichloromethane, chloroform, dichloroethane, acetonitrile, THF, 1,4-dioxane or toluene.

Further the invention provides use of a phosphonamidate compound to improve flame resistance, in particular in polyurethane foams.

Advantageous embodiments are defined in the dependent claims.

BRIEF DESCRIPTION OF THE DRAWINGS

The above mentioned and other features and objects of this invention and the manner of achieving them will become more apparent and this invention itself will be better understood by reference to the following description of various embodiments of this Invention taken in conjunction with the accompanying drawings, wherein are shown.

DETAILED DESCRIPTION OF THE INVENTION

Materials

Figure 1:
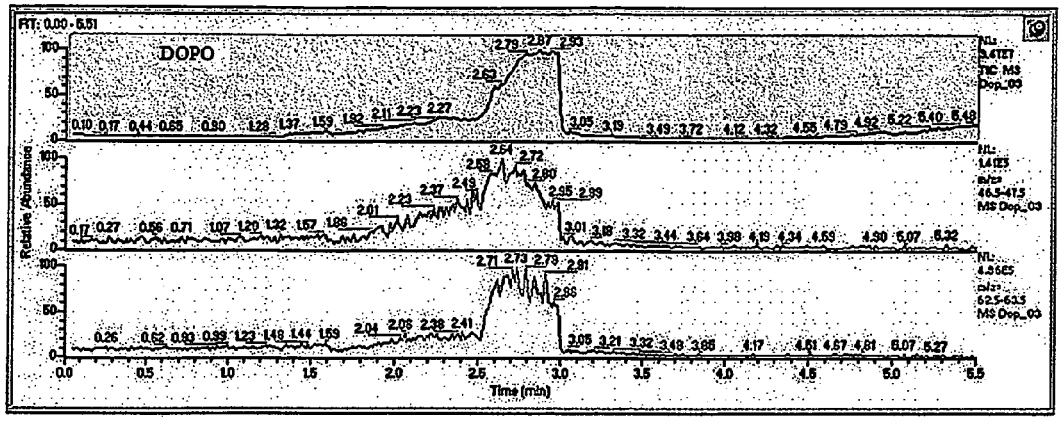
FIGS. 1 to 10 total ion chromatograms for a selection of amino-DOPO derivatives showing, as a function of time in minutes: total ion chromatogram (top trace), ion signal of PO radical at m/z=47 (middle trace) and ion signal of PO$_2$ radical at m/z=63 (bottom trace)
Figure 2:
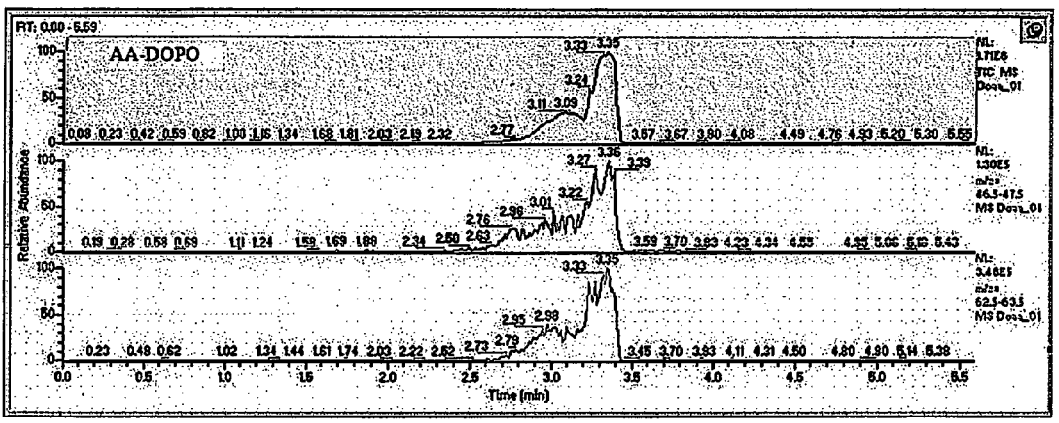
Figure 3:
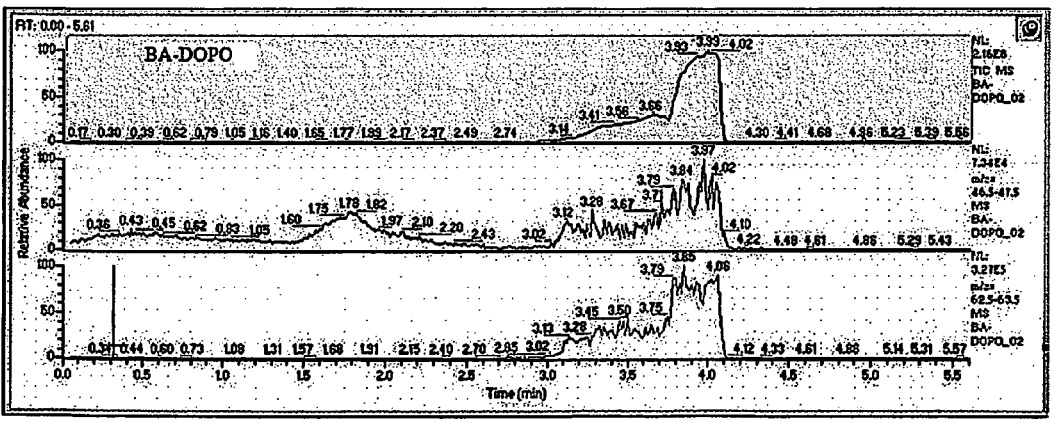
Figure 4:
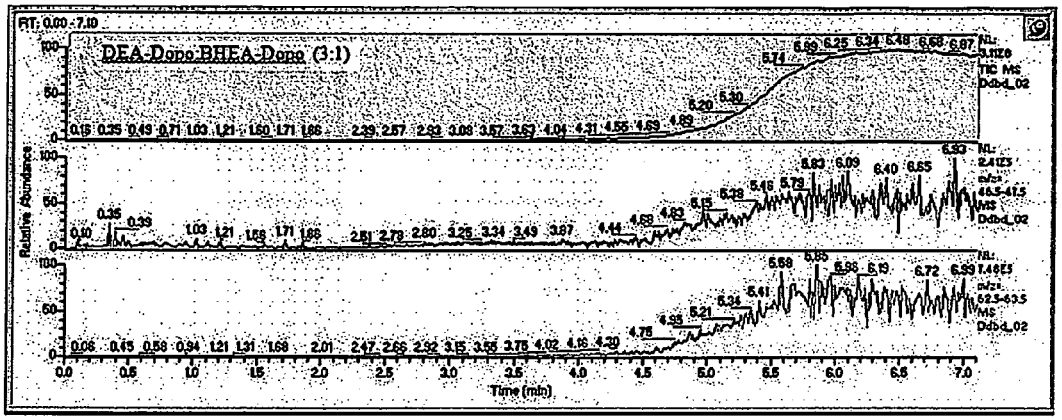
Figure 5:
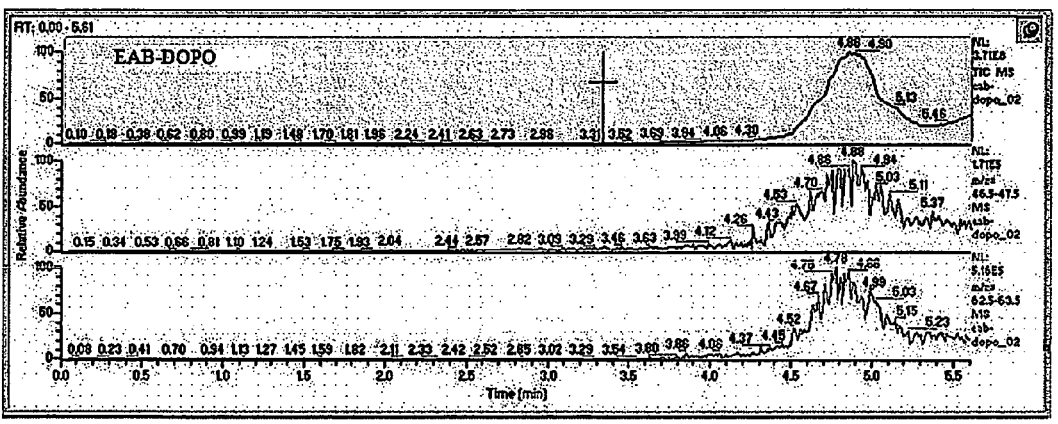
Figure 6:
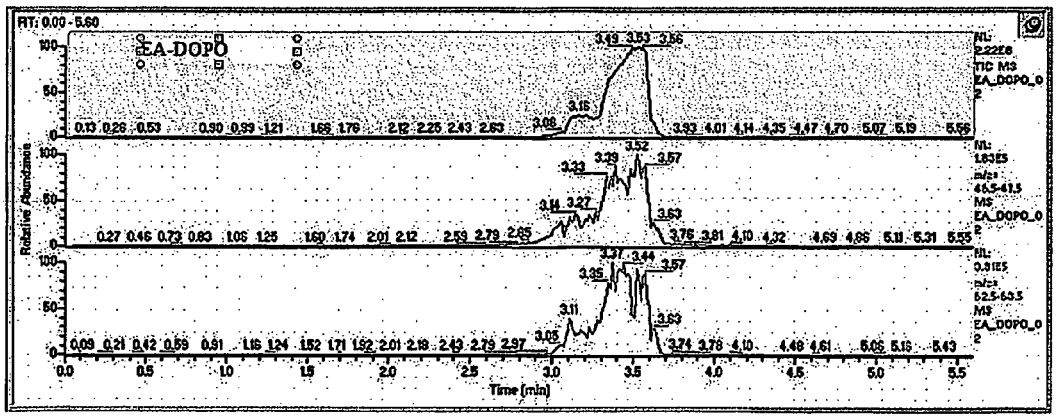
Figure 7:
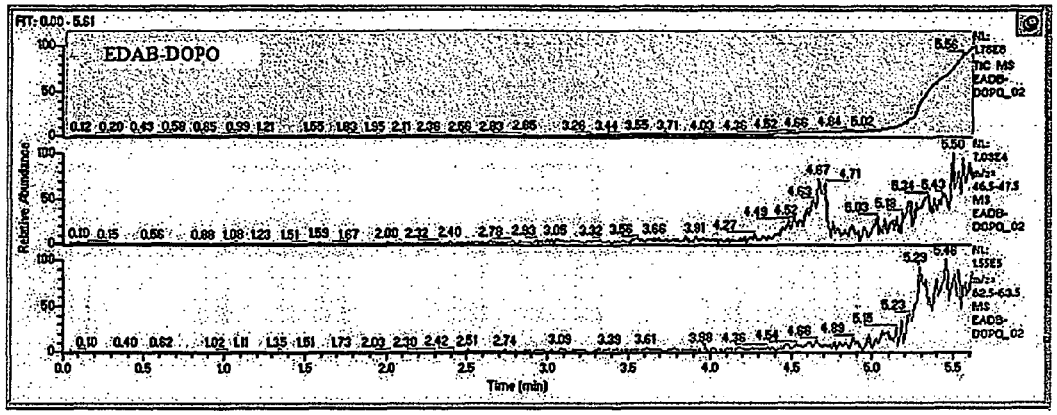
Figure 8:
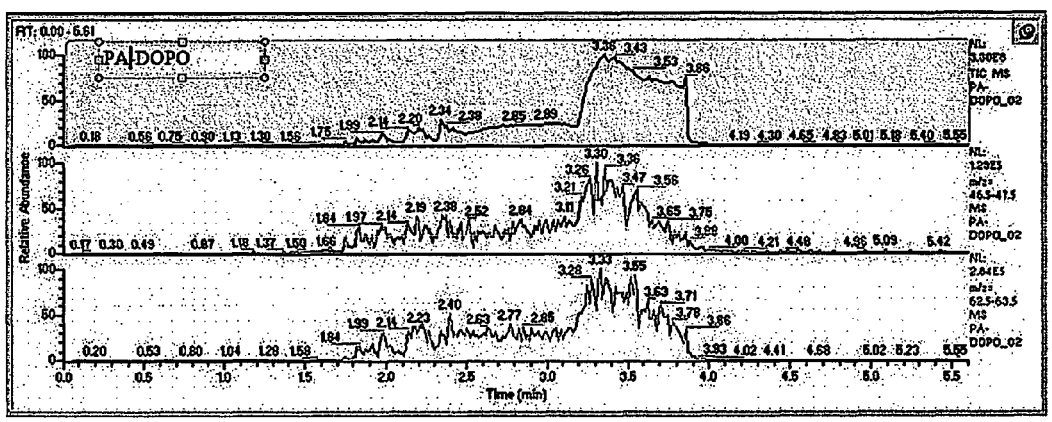
Figure 9:
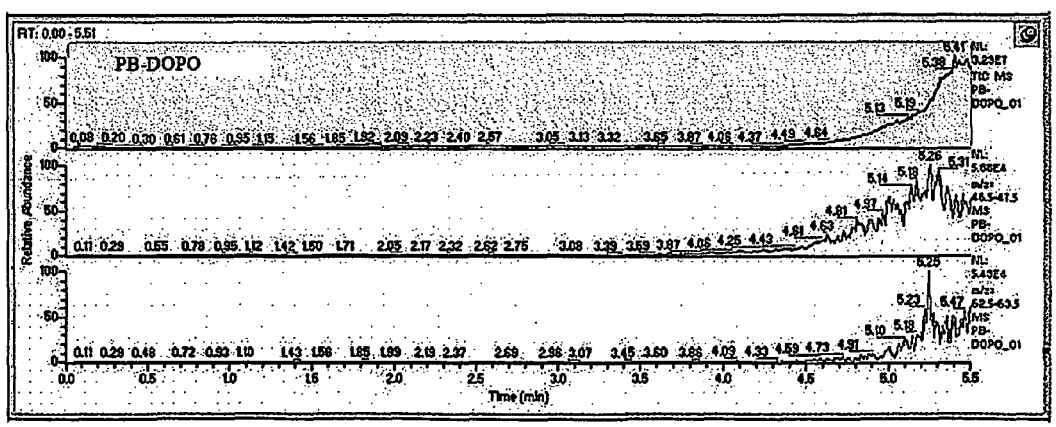
Figure 10:
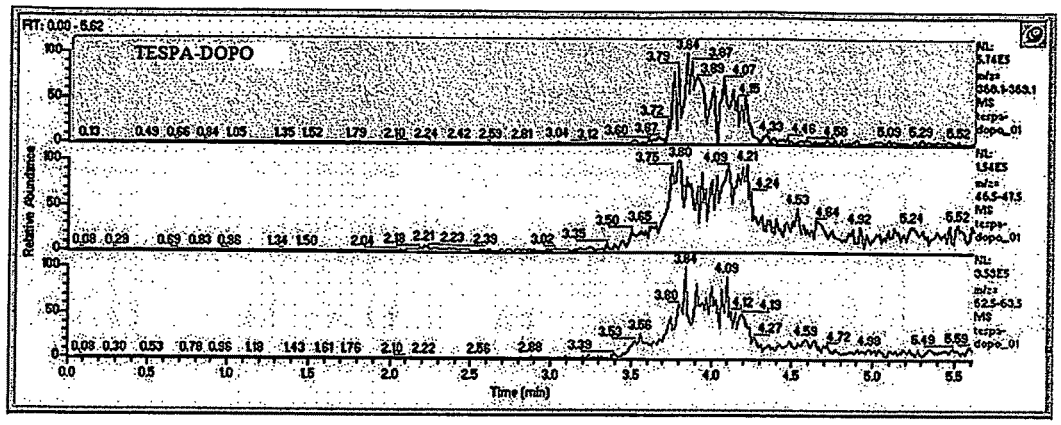

All reagents and solvents were reagent grade or were purified by standard methods before use. 9,10-Dihydro-9- oxa-10-phosphaphenanthrene-10-oxide (DOPO) was purchased from Conier Chem & Pharma Co., Ltd and used as received. The amines used were purchased from Aldrich and used as received. CCl$_4$ and Trichloroisocyanuric acid (TCCA) from Aldrich were used as chlorinating agents as received.

Syntheses

The amino-DOPO (phosphonamidates) were synthesized by two synthetic procedures as described hereinbelow.

General Procedure a for the Preparation of Amino-DOPO Derivatives (Phosphonamidates)

Scheme 4: General reaction scheme for the preparation of amino-DOPO derivatives via an Atherton-Todd-reaction

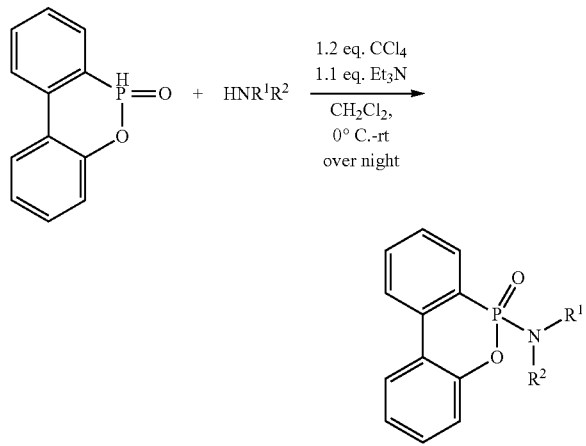

9,10-Dihydro-9-oxa-10-phosphaphenanthrene-10-oxide (DOPO) (108 g, 500 mmol), triethyl amine (79 ml, 566 mmol) and the appropriate amine (240-750 mmol) are dissolved in 400 ml of an appropriate solvent, for example dichloromethane, chloroform, dichloroethane, acetonitrile, THF, 1,4-dioxane or toluene, stirred and cooled to 0° C. After the solution has been cooled down, tetrachloro methane (59 ml, 600 mmol) is added dropwise at a rate that the reaction temperature does not exceed 10° C. After all tetrachloro methane has been added, the solution is allowed to warm up to room temperature and the stirring is continued until all the starting material has been consumed (observed with TLC). After complete conversion the triethylamine hydrochloride is filtered off and washed with excess of dichloromethane. The resulting clear solution is washed with water (100 ml), dried over Na$_2$SO4 and the solvent is evaporated in vacuum. If the resulting product does not exhibit enough analytical purity, it is recrystallized from an appropriate solvent.

General Procedure B for the Preparation of Amino-DOPO Derivatives (Phosphonamidates):

Scheme 5: General reaction scheme for the preparation of amino-DOPO using TCCA as chlorinating agent

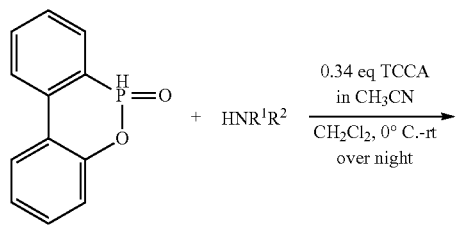

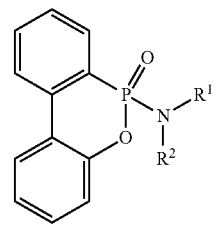

TCCA—trichloroisocyanuric acid 9,10-Dihydro-9-oxa-10-phosphaphenanthrene-10-oxide (DOPO) (108 g, 500 mmol), triethyl amine (79 ml, 566 mmol) and the appropriate amine (240-750 mmol) are dissolved in 400 ml of an appropriate solvent, for example dichloromethane, chloroform, dichloroethane acetonitrile, THF, 1,4-dioxane or toluene, stirred and cooled to 0° C. After the solution has been cooled down, a solution of TCCA (38.7 g, 166.7 mmol) in 200 ml acetonitrile is added dropwise at a rate that the reaction temperature does not exceed 10° C. After this solution has been added completely the solution is allowed to warm up to room temperature and stirring is continued until all the starting material has been consumed (TLC). After complete conversion the reaction mixture is filtered to remove of the triethylamine hydrochloride and cyanuric acid. The resulting clear solution is washed with water (100 ml). The aqueous phase is extracted twice with 100 ml dichloromethane. The combined organic phases are dried over Na$_2$SO$_4$ and the solvent is evaporated in vacuum. If the resulting product does not exhibit enough analytical purity, it is recrystallized from an appropriate solvent.

Analytical Data

Example 1

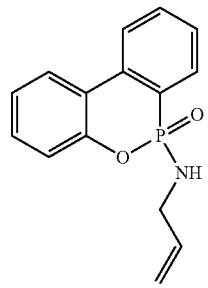

6-(allylamino)-6H-dibenzo[c,e][1,2]
oxaphosphinine 6-oxide
(AA-DOPO)

Synthesis run with a ratio of DOPO to amine: 1:1

Solvent: CH$_2$Cl$_2$

Yield: 119.2 g (440 mmol, 88%)

m.p. 95° C.

$^1$H-NMR (CDCl$_3$) δ (ppm): 7.88-7.99 (m, 3H), 7.92 (dd, J=1.7, 7.9 Hz, 1H), 7.66 (tt, J=1.3, 8.7, 1H), 7.48 (ddt, J=1.0, 3.0, 7.5 Hz, 1H), 7.35 (m$_c$, 1H), 7.20-7.26 (m, 2H), 5.75-5.86 (m, 1H), 5.19 (dq, J=1.4, 17.1 Hz, 1H), 5.06 (dq, J=1.4, 10.3 Hz, 1H), 3.39-3.60 (m, 3H).

$^{13}$C-NMR (CDCl$_3$) δ (ppm): 149.8, 138.9, 137.0, 132.7, 130.1, 130.0 128.4, 128.1 127.2, 124.8, 124.2, 123.5, 123.3, 121.9, 44.9.

$^{31}$P-NMR (CDCl$_3$) δ (ppm): 15.9.

IR (Film) ν (cm$^{-1}$)=3179 (m), 2855 (w), 1648 (w), 1592 (w), 1475 (m), 1428 (m), 1222 (s), 1198 (m), 1152 (m), 1142 (s), 1054 (w), 923 (m), 899 (w), 752 (s), 715 (s).

MS (ESI) m/z (%) 271 (14), 216 (55), 199 (18), 168 (54), 139 (27), 56 (100).

Example 2

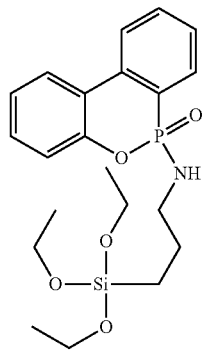

6-((3-(triethoxysilyl)propyl)amino)-6H-dibenzo[c,e][1,2]oxaphosphinine 6-oxide
(TESPA-DOPO)

One could imagine preparing DOPO-amino silane derivatives by choosing different kinds of functional silanes or siloxanes. Furthermore DOPO amino silane or siloxane derivatives can be further hydrolyzed and polymerized to form cross-linked or linear polymers as described for DOPO-phosphinates in literature.[12]

Synthesis run with a ratio of DOPO to amine: 1:1
Solvent: CH$_2$Cl$_2$
Yield: 7.57 g (17.4 mmol, 75%)
m.p.: 85° C.

$^1$H-NMR (CDCl$_3$) δ (ppm): 7.86-7.99 (m, 3H), 7.66 (tt, J=1.2, 8.8, 1H), 7.48 (ddt, J=0.8, 3.1, 7.5 Hz, 1H), 7.35 (m$_c$, 1H), 7.19-7.25 (m, 2H), 3.76 (q, J=6.9 Hz, 6H), 3.41 (m$_c$, 1H), 2.87 (m$_c$, 2H), 1.59 (m$_c$, 2H), 1.17 (t, J=6.9 Hz, 9H), 0.59 (m$_c$, 2H).

$^{13}$C-NMR (CDCl$_3$) δ (ppm): 150.1, 137.2, 132.8, 130.3, 130.2 128.2, 125.5, 125.0, 124.3, 123.8, 123.7, 122.2, 120.7, 58.5, 43.6, 25.1, 18.4, 7.5.

$^{31}$P-NMR (CDCl$_3$) δ (ppm): 15.8.

IR (Film) ν (cm$^{-1}$)=3148 (w), 2939 (w), 2895 (w), 2838 (w), 1597 (w), 1474 (m), 1430 (m), 1274 (w), 1225 (m), 1195 (s), 1149 (m), 1074 (s), 926 (m), 816 (m), 752 (s).

Example 3

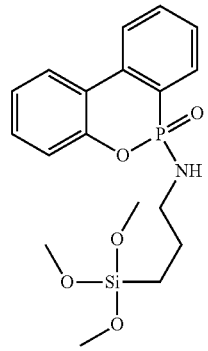

6-((3-(trimethoxysilyl)propyl)amino)-6H-dibenzo[c,e][1,2]oxaphosphinine 6-oxide
(TMSPA-DOPO)

Synthesis run with a ratio of DOPO to amine: 1:1
Solvent: CH$_2$Cl$_2$
Yield: 161 g (370 mmol, 74%)
m.p.: 85° C.

$^1$H-NMR (CDCl$_3$) δ (ppm): 7.86-7.99 (m, 3H), 7.66 (tt, J=1.2, 8.8, 1H), 7.48 (ddt, J=0.8, 3.1, 7.5 Hz, 1H), 7.35 (m$_c$, 1H), 7.19-7.25 (m, 2H), 3.55 (m$_c$, 1H), 3.49 (s, 9H), 2.87 (m$_c$, 2H), 1.58 (m$_c$, 2H), 0.59 (m$_c$, 2H).

$^{31}$P-NMR (CDCl$_3$) δ (ppm): 15.8.

Example 4

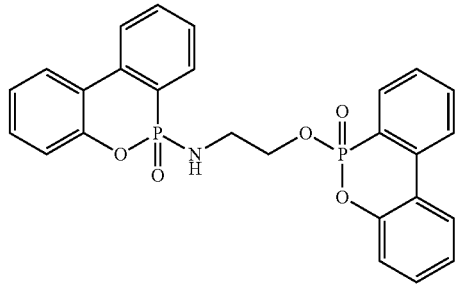

6-(2-((6-oxido-6H-dibenzo[c,e][1,2]oxaphosphinin-6-yl)amino)ethoxy)-6H-dibenzo[c,e][1,2]oxaphosphinine 6-oxide
(EAB-DOPO)

Synthesis run with a ratio of DOPO to amine: 2:1
Solvent: CH$_2$Cl$_2$
Yield: 98.2 g (203 mmol, 81%)
m.p. 121° C.

$^1$H-NMR (CDCl$_3$) δ (ppm): 7.85-7.99 (m, 5H), 7.71-7.85 (m, 2H), 7.65 (m$_c$, 1H), 7.48-7.56 (m, 1H), 7.32-7.45 (m, 3H), 7.10-7.28 (m, 4H), 4.16 (m$_c$, 2H), 3.51 (m$_c$, 1H), 3.17 (m$_c$, 2H).

$^{13}$C-NMR (CDCl$_3$) δ (ppm): 149.8, 149.7, 137.2, 137.1, 133.9, 133.1, 130.8, 130.5, 130.5, 130.4, 130.1, 128.6, 128.4, 125.5, 125.5, 125.1, 124.5, 124.3, 123.8, 122.6, 122.1, 120.7, 120.3, 120.2, 66.9, 41.4

$^{31}$P-NMR (CDCl$_3$) δ (ppm): 15.5 (d, J=3.5 Hz, 1P), 11.4.

IR (Film) ν (cm$^{-1}$)=3215 (w), 2879 (w), 1597 (w), 1476 (m), 1430 (m), 1267 (m), 1230 (m), 1204 (s), 1151 (m), 1118 (m), 1029 (m), 989 (m), 911 (s), 749 (s).

MS (ESI) m/z (%) 489 (100).

Examples 5, 6, 7

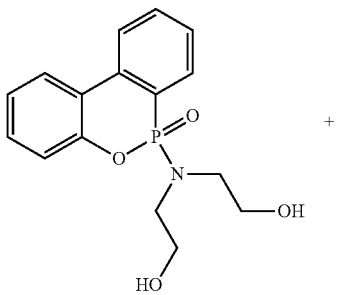

6-(bis(2-hydroxyethyl)amino)-6H-
dibenzo[c,e][1,2]oxaphosphinine 6-oxide
(BHEA-DOPO)

+

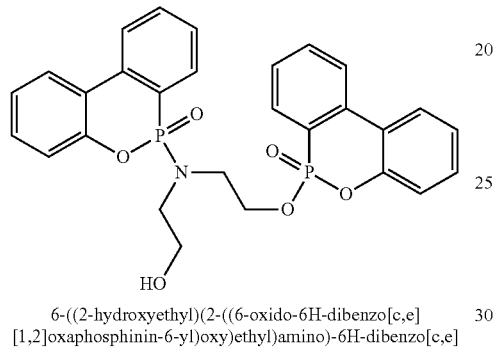

6-((2-hydroxyethyl)(2-((6-oxido-6H-dibenzo[c,e]
[1,2]oxaphosphinin-6-yl)oxy)ethyl)amino)-6H-dibenzo[c,e]
[1,2]oxaphosphinine 6-oxide
(DEA-DDOPO)

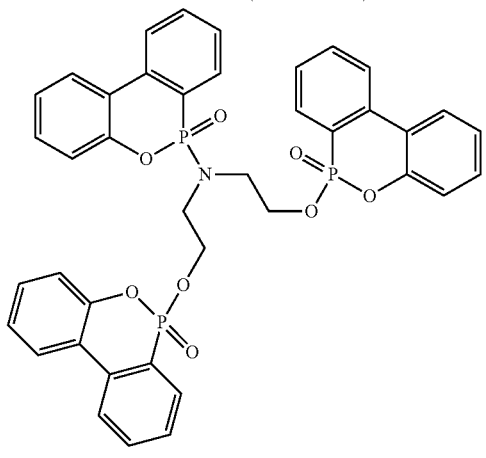

6,6'-(((((6-oxido-6H-dibenzo[c,e][1,2]oxaphosphinin-6-
yl)azanediyl)bis(ethane-2,1-diyl))bis(oxy))bis(6H-
dibenzo[c,e][1,2]oxaphosphinine 6-oxide)
(DEA-TDOPO)

Synthesis run with a ratio of DOPO to amine: 1:1 or 1:1.5
Solvent: $CH_2Cl_2$
Yield: 113.2 g (355 mmol, 71%)
HPLC-MS (ESI-MS): retention time BHEA-DOPO 15.2 min (319.9 m/z), DEA-DOPO 15.7 min (533.9 m/z); Flow 0.25 ml/min, solvent mixture 90:10 $H_2O$+0.1% formic acid: acetonitrile+0.1% formic acid for 1 minute, then gradient to 0:100 within 10 minutes, then two more minutes 0:100, then gradient to 90:10 within two minutes, 5 minutes isocratic at 90:10. Column: Phenomenex® Gemini C18, 110A, 250 mm*2 mm*5 μm.

Reaction of DOPO with diethanolamine (DEA) can result in three kinds of molecules i.e. BHEA-DOPO, DEA-DDOPO, DEA-TDOPO. In the synthesis described in our experiment leads to compounds BHEA-DOPO and DEA-DDOPO in the ratio 1:3 respectively. One could Imagine preparing DEA-TDOPO by varying the reaction conditions. It is also possible to prepare one the above mentioned compounds exclusively by optimizing the reaction conditions.

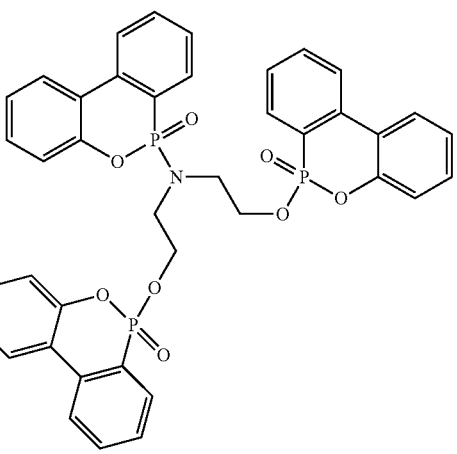

6,6'-(((((6-oxido-6H-dibenzo[c,e][1,2]oxaphosphinin-6-
yl)azanediyl)bis(ethane-2,1-diyl))bis(oxy))bis(6H-
dibenzo[c,e][1,2]oxaphosphinine 6-oxide)
(DEA-TDOPO)

Analytical Data for DEA-TDOPO
$^1$H-NMR (CDCl$_3$) δ (ppm): 7.80-8.05 (m, 9H), 7.65-7.80 (m, 3H), 6.95-7.45 (m, 12H), 4.01-4.18 (m, 4H), 3.0-3.21 (m, 4H).
$^{31}$P-NMR (Trifluoroethanol-d$^3$) δ (ppm): 16.9, 10.7.
MS (ESI) m/z (%) 747 (100).

Example 8

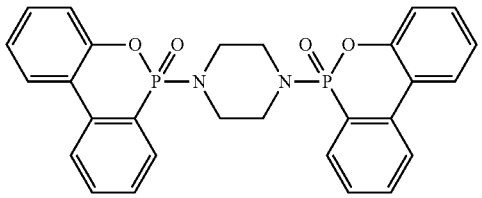

6,6'-(piperazine-1,4-diyl)bis(6H-
dibenzo[c,e][1,2]oxaphosphinine 6-
oxide)
(PB-DOPO)

Synthesis run with a ratio of DOPO to amine: 2.5:1
Solvent: $CHCl_3$
Yield: 110.5 g (212 mmol, 85%)
m.p. 320° C.
$^1$H-NMR (Trifluoroethanol-d$^3$) δ (ppm): 7.91 (m$_c$, 2H), 7.84 (m$_c$, 2H), 7.56-7.66 (m, 4H), 7.38 (m$_c$, 2H), 7.24 (m$_c$, 2H), 7.12 (m$_c$, 2H), 7.06 (m$_c$, 7.06), 2.99 (m$_c$, 8H).

$^{13}$C-NMR (Trifluoroethanol-d$^3$) δ (ppm): 151.2, 139.8, 136.0, 132.6, 131.2, 130.6, 127.0, 126.1, 123.5, 123.4, 121.9, 121.8, 45.7.

$^{31}$P-NMR (Trifluoroethanol-d$^3$) δ (ppm): 19.5.

IR (Film) ν (cm$^{-1}$)=2856 (w), 1596 (w), 1476 (w), 1428 (w), 1369 (w), 1230 (s), 1205 (m), 1147 (m), 1114 (m), 969 (m), 901 (s), 747 (s), 707 (s).

MS (ESI) m/z (%) 514 (100).

Example 9

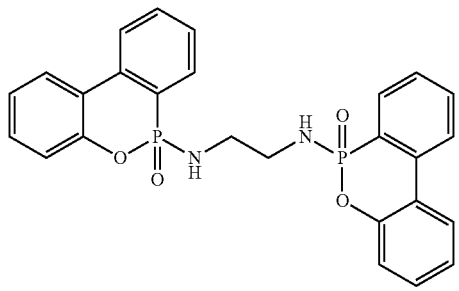

6,6'-(ethane-1,2-diylbis(azanediyl))bis(6H-dibenzo[c,e][1,2]oxaphosphinine 6-oxide)
(EDAB-DOPO)

Synthesis run with a ratio of DOPO to amine: 2.5:1
Solvent: CHCl$_3$
Yield: 102.5 g (210 mmol, 84%)
m.p. 267-270° C.

$^1$H-NMR (Trifluoroethanol-d$^3$) δ (ppm): 7.65-7.75 (m, 3H), 7.54-763 (m, 2H), 7.40-7.52 (m, 3H), 7.26-7.33 (m$_c$, 1H), 6.97-7.19 (m, 5H), 6.81 (dd, J=1.1, 7.9 Hz, 1H), 7.59 (dd, J=1.1, 8.0 Hz, 1H), 2.73-2.91 (m, 2H), 2.58-2.72 (m, 2H).

$^{13}$C-NMR (Trifluoroethanol-d$^3$) δ (ppm): 150.8, 150.5, 139.3, 139.1, 135.8, 135.7, 132.5, 132.4, 131.4, 131.3, 130.3, 130.2, 126.8, 126.7, 126.1, 125.8, 123.3, 123.2, 121.8, 121.5, 43.6, 43.4.

$^{31}$P-NMR (Trifluoroethanol-d$^3$) δ (ppm): 21.4, 20.7.

IR (Film) ν (cm$^{-1}$)=3159 (m), 2877 (w), 1598 (w), 1476 (m), 1446 (m), 1196 (s), 1146 (m), 1116 (s), 922 (s), 747 (s), 711 (m).

MS (ESI) m/z (%) 488 (100).

Example 10

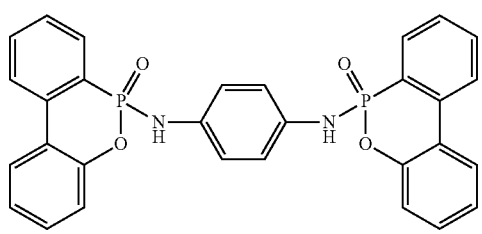

6,6'-(1,4-phenylenebis(azanediyl))bis(6H-dibenzo[c,e][1,2]oxaphosphinine 6-oxide)
(PDAB-DOPO)

Synthesis run with a ratio of DOPO to amine: 2.5:1
Solvent: CHCl$_3$
Yield: 5.2 g (9.7 mmol, 81%)
m.p. 295° C. (decamp.)

$^1$H-NMR (trifluoroethanol-d$^3$) δ (ppm): 7.75-7.90 (m, 4H), 7.51-7.65 (m, 4H), 7.27 (m$_c$, 2H), 7.21 (m$_c$, 2H), 7.11 (m$_c$, 2H), 7.01 (d, J=8.1 Hz, 2H) 6.54 (s, 4H).

$^{31}$P-NMR (CDCl$_3$) δ (ppm): 14.9.

IR (Film) ν (cm$^{-1}$)=3153 (w), 3093 (w), 2944 (w), 1506 (m), 1477 (m), 1392 (w), 1286 (m), 1196 (s), 1116 (w), 974 (s), 911 (w), 747 (s).

MS (ESI) m/z (%) 536 (100).

Example 11

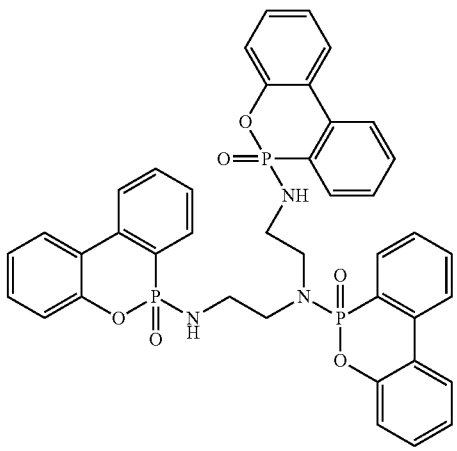

6-((3-((6-oxido-6H-dibenzo[c,e][1,2]oxaphosphinin-6-yl)(2-((6-oxido-6H-dibenzo[c,e][1,2]oxaphosphinin-6-yl)amino)ethyl)amino)propyl)amino)-6H-dibenzo[c,e][1,2]oxaphosphinine 6-oxide
TDETA-DOPO Synthesis run with a ratio of DOPO to amine: 3.5:1
Solvent: CHCl$_3$
Yield: 102.5 g (210 mmol, 84%)
m.p. 267-270° C.

$^1$H-NMR (CDCl$_3$) δ (ppm): 7.65-7.95 (m, 9H), 7.40-7.63 (m, 3H), 6.82-7.35 (m, 12H), 3.99 (bs, 3H), 3.1-3.25 (m, 4H), 2.98-3.10 (m, 4H).

$^{31}$P-NMR (Trifluoroethanol-d$^3$) δ (ppm): 15.9, 17.8

MS (ESI) m/z (%) 745 (100).

Example 12

As an example for the preparation of multi-DOPO derivatives of tetraethylenepentaamine, an amount of tetraethylenpentaamine was reacted with an excess of DOPO. This reaction resulted in a mixture of poly-DOPO amino derivatives which were identified by HPLC-MS. HPLC-MS data of these mixtures indicates that tetraethylenepentaamine had 3-5 DOPO attached to various amino groups. This mixture could be considered as an oligomeric mixture that does not have to pass the REACH regulations. Scheme shown below shows tetraethylenepentaamine DOPO (TEPA-PDOPO) derivative where all amino groups have been reacted with DOPO.

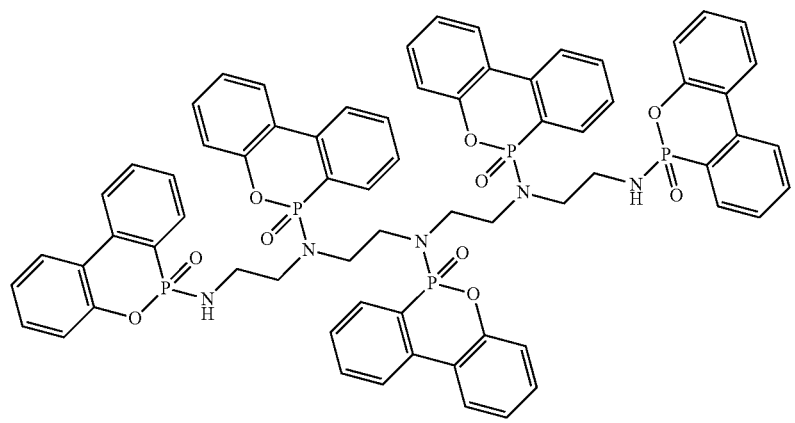

6,6'-((((6-oxido-6H-dibenzo[c,e][1,2]oxaphosphinin-6-yl)azanediyl)bis(ethane-2,1-diyl))bis((2-((6-oxido-6H-dibenzo[c,e][1,2]oxaphosphinin-6-yl)amino)ethyl)azanediyl))bis(6H-dibenzo[c,e][1,2]oxaphosphinine 6-oxide)-(TEPA-PDOPO)
HPLC-MS: m/z = 1260

Proof of Gas Phase Action of Amino-DOPO Derivatives

DOPO and its phosphinate derivatives have been known to exhibit Gas phase action. There exist analytical data which clearly indicates the formation of PO* radical which can quench the H* and OH* radicals formed during the thermal decomposition of polymers and prevent their oxidation.[4a,5] There exists no analytical data for the gas phase action of the amino-DOPO derivatives. Thus in this work elucidation of gas phase action of the amino derivatives of DOPO was carried out using direct insertion probe MS. The amino DOPO derivatives were heated from 50° C. to 450° C. at a rapid rate of 100° C./min in a quartz capillary in the ion source of MS and held for further 2 mins and various mass fragments measured. The total ion chromatograph (TIC) was then scanned for PO* (m/z 47) and $PO_2$ (m/z 63). FIGS. 1 to 10 show the TIC chromatogram for each amino-DOPO derivatives.

The above figures clearly indicates the gas phase action of amino-DOPO derivatives as all of them exhibit PO* (m/z 47) and $PO_2$ (m/z 63) release at elevated temperature. Furthermore it is also evident that the formation of these active species happens at different temperatures (indicated by time of formation) for different derivatives and thus could imply different application areas (i.e. different polymeric systems).

Thermal Stabilities of DOPO Derivatives

Figure 11:
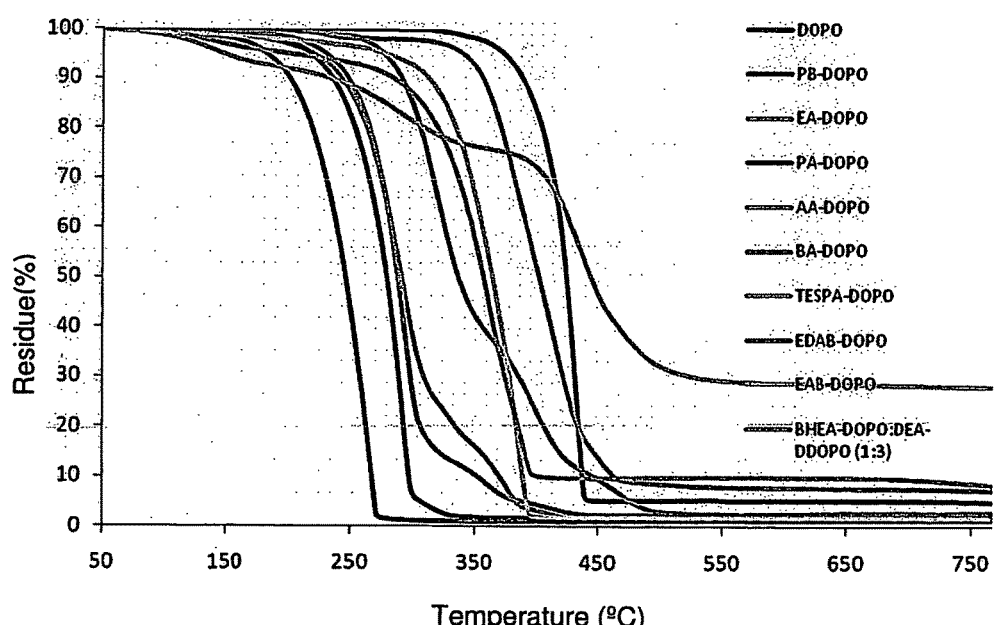
FIG. 11 thermal gravimetric data for a selection of amino-DOPO derivatives showing percentage of residue as a function of temperature in ° C.

One of the important objectives of developing various amino derivatives of DOPO was to improve the thermal stability of DOPO itself. This will ensure their suitability to be used in thermoplastic polymers which require usually high processing temperatures (200-350° C.). The thermal decomposition studies of DOPO and DOPO derivatives are shown in FIG. 11.

Various transition temperatures and char content of amino derivatives of DOPO is further tabulated in Table 1.

TABLE 1

TGA data of Amino DOPO derivatives

| Compounds | $T_{d1}$ (° C.) | $T_{dMax}$ (° C.) | % Char at 800° C. |
|---|---|---|---|
| DOPO | 201 | 267 | 2 |
| BHEA-DOPO:DEA-DDOPO (1:3) | 284 | 361 | 8 |

TABLE 1-continued

TGA data of Amino DOPO derivatives

| Compounds | $T_{d1}$ (° C.) | $T_{dMax}$ (° C.) | % Char at 800° C. |
|---|---|---|---|
| EDAB-DOPO | 355 | 415 | 7 |
| PA-DOPO | 235 | 292 | 2 |
| AA-DOPO | 247 | 295 | 3 |
| PB-DOPO | 387 | 433 | 5 |
| BA-DOPO* | 289 | 315/400/462 | 2 |
| TESPA- DOPO* | 234 | 135/287/437 | 28 |
| EAB-DOPO | 311 | 387 | 2 |
| EA-DOPO* | 241 | 293/375 | 2 |
| TDETA-DOPO | 294 | 385 | 2 |

$T_{d1}$: Temperature for 10% weight loss,
$T_{dMax}$: Temperature for maximum decomposition rate,
*Multiple decomposition stages, Bold data indicates main stage of decomposition.

It can be observed from the FIG. 11 and table 1 that DOPO starts to decompose earlier than 200° C. and thus not very suitable for melt processing of most organic polymers. Most of the amino DOPO derivatives are quite stable at this temperature and thus more suitable for melt processing at temperatures >200° C. Furthermore some derivatives such as PB-DOPO and EDAB-DOPO have stabilities above 300° C.

No previous studies on amino DOPO derivatives indicate their thermal stabilities. It can also be seen from the TGA data that TESPA-DOPO has a very interesting thermal behavior. It has relatively very high char content of (28%) at 800° C. and indicates possible hybrid action i.e. combined gas phase and condensed phase action. This kind of hybrid flame retardant can find useful applications in special intumescent coatings.

Water Solubility of Specific DOPO Compounds

These DOPO-derivatives are very barely soluble in water as it is exemplarily shown for EDAB-DOPO and TEPA-PDOPO in table 2.

TABLE 2

Water solubility of EDAB-DOPO and TEPA-PDOPO

| Flame retardant | Temperature | solubilitiy FR in water mg/L | solubilitiy FR in water mmol/L |
|---|---|---|---|
| EDAB-DOPO | 25° C. | 392.9 | 0.80 |
| EDAB-DOPO | 90° C. | 500.8 | 1.03 |
| TEPA-PDOPO | 25° C. | 15.4 | 0.01 |
| TEPA-PDOPO | 90° C. | 818.1 | 0.65 |

From table 2 it can be seen that only very small amounts of EDAB-DOPO and TEPA-PDOPO dissolve in water even when the temperature is raised to 90° C.

This fact makes these compounds very useful for different flame retardant applications where one requirement is the solubility in any organic solvent and limited solubility in water.

Application and Test Procedures

The synthesized compounds were evaluated for flame retardant properties by incorporating them in flexible PU foams.

Methods for the manufacture of flexible polyurethane foams (flexible PU foams) are known in the art and are covered, for example, on pages 163-197 of the Plastics Manual, Volume 7, Polyurethanes, Becker/Braun, first edition (1985), published by Carl Hanser Verlag.

Conventionally, flexible PU foam may be made by reacting a polyol with a multifunctional isocyanate so that NCO and OH groups form urethane linkages by an addition reaction, and the polyurethane is foamed with carbon dioxide produced in situ by reaction of isocyanate with water.

This conventional process may be carried out as a so-called 'one-shot' process whereby the polyol, isocyanate and water are mixed together so that the polyurethane is formed and foamed in the same step.

The flexible polyurethane foams were manufactured according to the recipe mentioned in Table 3 below.

The manufacture of the foams according to the formulations in Table 3 was done by handmix in the laboratory based on 200 gms polyol. The formulation of the components taking part in the reaction was identical in all cases except for the addition of Flame retardants where indicated.

TABLE 3

Flexible Polyurethane (PU) foam formulation
Flexible PU Foam

| Ingredients | pphp |
|---|---|
| All PO polyol | 97 |
| Compatibilizers | 3.4 |
| Tin(II)octanoate | 0.25 |
| Catalysts | 0.5 |
| Silicone Stabilizer | 0.5 |
| H$_2$O (total) | 1.85 |
| Toluene diisocyante (TDI) | 29.8 |
| Flame Retardant (FR) | X |

X = 1-30%

Description of the Ingredients:

With regard to the polyol this may be of any suitable kind. Typically polyether and polyester polyols are used in the production of PU foam and in accordance with the present invention. In table 3 the polyol is a polyether polyol. Where a polyether polyol is used this is preferably wholly or predominantly propylene oxide (PO) derived, although ethylene oxide (EO) may also be used instead of, or additionally to PO. However it is also possible to use polyester polyol or mixtures of polyether and polyester polyol. Suitable polyols may have an OH functionality of 2 to 6, particularly 2 to 4 and may have a molecular weight (MW) in the range say 400-10,000.

It is well known in the art to use mixed polyols to vary the reactivity of the system or impart desired properties to the resulting PU foam and, with the present invention, whilst PO derived polyether polyol is generally preferred, other polyols and mixtures of polyols may be used as required.

Examples of the polyether polyols that can be used according to the invention are described, for example, on pages 44-54 and 75-78 of the Plastics Manual, Volume 7, Polyurethanes, Becker/Braun, 2$^{nd}$ edition, published by Carl Hanser Verlag.

Thus, for example, polyol may be as follows:
I. derived from PO and propyleneneglycol with viscosity (at 25° C.) of 250-350 mPa·s, OH number 56±3.
II. derived from EO and PO and trimethylolpropane with viscosity (at 25° C.) 750-900 mPa·s, OH number 35±2.
III. derived from PO and trimethylolpropane with viscosity 600-700, OH number 380±25.
IV. derived from PO and glycerine with viscosity 450-550 and OH number 56±3.

All viscosity measurements (in mPa·s) are obtained using a Brookfield Viscometer. Unless otherwise stated viscosity is measured at 25 EC. The OH number (hydroxyl number) is a conventional parameter which gives the concentration of NCO-reactive OH groups per unit weight in mg KOH/g.

$$\text{Hydroxyl number (OH)} = \frac{56.1 \times \text{functionality}}{\text{MW polyol}} \times 1,000$$

It is also possible to use those polyether polyols which already contain built-in catalysts, as for example described in WO 03/016373A1. It is likewise also possible to use mixtures of the aforementioned polyether polyols.

The invention can also be applied to OH terminated prepolymer foams, Natural oil based polyols (NOP's), mixtures and/or prepolymers thereof.

The polyol described in table 2 is a triol which is a propylene oxide adduct of glycerine and has a molecular weight of the order of 3,000. Commercial examples are Voranol® 3008 (Dow Chemical Company), or DESMOPHEN® 20WB56 (Bayer).

With regard to the multifunctional isocyanate this is preferably a diisocyanate, particularly TDI (toluene diisocyanate) AS described in table 2 However other multifunctional isocyanates, preferably having a functionality of 2 to 5 may be used alone or in any suitable combination. Thus the multifunctional isocyanate may be any one or more of:

TDI (all isomer blends of toluene diisocyanate),
MDI (methylene diphenyl isocyanate),
Which may be pure or polymeric versions (so called aromatic isocyanates).

More particularly, the multifunctional isocyanate is a polyisocyanate containing two or more isocyanate groups and standard commercial di- and/or triisocyanates are typically used. Examples of suitable ones are aliphatic, cycloaliphatic, arylaliphatic and/or aromatic isocyanates, such as the commercially available mixtures of 2,4- and 2,6-isomers of diisocyanatotoluene (=tolylenediisocyanate TDI), which are marketed under the trade names Caradate® T80 (Shell) or Voranate® T80 and T65 (Dow Chemicals). 4,4'-diisocyanatodiphenylmethane (=4,4'-methylenebis(phenylisocyanate); MDI) and mixtures of TDI and MDI can also be used.

It is also possible, however to use isocyanate prepolymers based on TDI or MDI and polyols. Modified or mixed isocyanates (for example Desmodur® MT58 from Bayer) may also be used. Examples of aliphatic isocyanates are 1,6-hexamethylene diisocyanates or triisocyanates such as Desmodur® N100 or N3300 from Bayer.Isocaynate index can be used from very low (75 or less) to very high (125 or above) to suit required hardness or other properties of the foam.

Catalysts can be those well known in the PU foaming art, in particular an amine such as DMEA (dimethyl ethanolamine), DABCO® 33 LV (a tertiary amine from Air Products). Low emission/reactive amines can also be used as catalysts. Example are Tegomanin ZE-1 from Evonik or Niax EF 700 from Momentive or NE 400 from Air Products.

A metallo-organic compounds such as a tin catalyst e.g. KOSMOS 29 (stannous octoate) but other low emission catalyst such as Kosmos EF (Tin Ricinolate), zinc octoaote or bismuth compounds be us can also be used.

Silicone stabilizers known in the art, for example silicone surfactant such as from the Tegostab® range from Evonik ie Tegostab B 8232, BF 2370 . . . or the Niax® range from Momentive ie L 670, L 595.

Additional additives like Compatibilizers (ie Silbyk 9904 from Byk Chemie), chain extending agents and/or cross-linking agents, such as diethanolamine, glycerine, sorbitol; as well as additional flame retardants; fillers can also be added to the formulation. Those additives and others known in the art in relation to conventional foaming processes may be used in any combination.

Water can be used in any amount suitable to achieve desired density (typically 0.1 to 15 pphp, preferably 1 to 5 pphp) also in combination with liquid CO2.

For comparison of the efficiency of the synthesized amino-DOPO derivatives, Tris(2-chlorisopropyl)phosphate (TCPP) which is commonly used flame retardant for foams was taken as standard FR. It is common in PU foam industry to use haloalkyl derivatives as flame retardant additives. Recently use of some of these derivatives as flame retardants [TCEP (tris(2-chloroethyl phosphate)), TDCPP (tri(2,3-dichloropropyl) phosphate) and TCPP)] have either been banned or being investigated for toxicity by environmental agencies.[13]

The resulting foams were dried and aged for 3 h at 80° C. The foams were then tested for their flammability according to Swiss flammability standard (BKZ). It's a vertical burning test for foamed materials with a specific sample size (length: 160 mm, width: 60 mm, thickness: 6 mm±10% tolerance). For each specimen flame test (BKZ) was performed in triplicate. If the results were not consistent, each specimen was tested 6 times. For the BKZ test an air dried specimen was placed in a vertical position and subjected to flame from the lower front edge by a standardized flame. The flame height of 20 mm was maintained and should burn constantly with sharp outlines. The burner position was adjusted 45° so that the flame hits the specimen vertically in the middle of the lower front edge. The flame is brought in contact with the foam for 15 sec and should be placed such that the foam bottom is approximately 4±1 mm inside the flame from the tip. The analysis of the burning test is then made according to the details given in Table 4.

TABLE 4

BKZ flammability test

| Classification | Requirements |
| --- | --- |
| Degree of flammability (Class 3) | time 5-20 s |
| Degree of flammability (Class 4) | time, duration of burning > 20 s |
| Degree of flammability (Class 5)* | flame does not reach the top level of the sample holder (150 mm). duration ≤ 20 s |

The BKZ-burning test was performed according to the procedure given above and the results are given in Table 5.

TABLE 5

Fire test on flexible PU foams-BKZ test

| FR | Amount | Classification[b] |
| --- | --- | --- |
| DOPO | 5% | Class 5 |
| BHEA-DOPO:DEA-DDOPO (1:3) | 5% | Class 5 |
| EDAB-DOPO | 5% | Class 5 |
| AA-DOPO | 5% | Class 5 |
| PB-DOPO | 5% | Class 5 |
| TCPP | 5% | Class 5 |
| TDETA-DOPO | 5% | Class 5 |
| TEPA-PDOPO | 5% | Class 5 | a) Classification according to table 1.
[b]virgin foam does not self-extinguish

These foams were also evaluated for flame retardancy (UL-94 HB test) using standard ASTM D4986 or ISO/DIS 9772.3. The data of such fire test is shown in Table 6 below:

TABLE 6

UL-94 HB test:

| Samples | Burning Rate (mm/min) | Rating[a] |
| --- | --- | --- |
| Blank | 58 | x |
| 5% DOPO | 48 | HBF |
| 5% AA-DOPO | 47 | HF-2 |
| 5% PB-DOPO | 57 | HBF |
| 5% EDAB-DOPO | 25 | HF-1 |
| 5% DEA-DOPO:BHEA-DOPO (3:1) | 52 | HF-2 |
| 5% TDETA-DOPO | not determined | HF-1 |
| 5% TEPA-PDOPO | not determined | HF-1 |
| 5% TCPP | 23 | HBF |

[a]x = foam does not self extinguish; HBF = Doesn't have any specimens with a burning rate exceeding 40 mm per minute over a 100 mm span, or have each specimen cease to burn before flaming or glowing reaches the 125 mm gauge mark; HF-2 = foam self extinguishes within two seconds after the burner has been removed, foam is damaged <60 mm, after glow time is less than 30 s, cotton indicator is allowed to be ignited by dripping, HF-1 = foam self extinguishes within two seconds after the burner has been removed, foam is damaged <60 mm, after glow time is less than 30 s, cotton indicator is not allowed to be ignited by dripping All amino-DOPO derivatives have similar or even better fire performance as compared to TCPP and hence can be used to replace TCPP as a halogen free FR system for flexible PU foams. It can be further observed from the Table 6 that amino derivatives of DOPO [AA-DOPO, EDAB-DOPO, DEA-DOPO: BHEA-DOPO (3:1)] have better flame retardancy effect as compared to unmodified DOPO. Without being bound by theory, it is contemplated that the enhanced flame retardancy effect of amino DOPO derivatives could be due to a P—N synergism effect.

Further tests were run to further investigate the effect of this new class of compounds.

Polyether Foams/EDAB-DOPO

The foams were produced in a standard commercial flexible foam slab stock plant (Messrs. Hennecke, Germany)

in a one-shot process. In this example the basic materials (raw materials) were metered according to the formulation directly from storage vessels into a mixing chamber by means of pumps (e.g. piston or gear pumps), the mixing chamber being equipped with an agitator and a discharge pipe.

The metering and mixing of the raw materials was done in a manner known in the art. In this example the temperature of the raw materials was run at 25±3° C.

The polyol output overall was 30 kg/min. EDAB-DOPO was pre-dispersed in the polyol before running the formulation in the one shot process.

TABLE 7

Evaluation of EDAB-DOPO in Polyether foams.

|  | 1 | 2 | 3 | 4 | 5 |
|---|---|---|---|---|---|
| Ref.VA 1812 | V06 | V01 | V02 | V16 | V14 |
| Polyol OH 56 all PO | 100 | 100 | 100 | 100 | 100 |
| TDI 80/20 | 26.2 | 26.2 | 38.8 | 26.2 | 38.8 |
| Water | 1.6 | 1.6 | 2.8 | 1.6 | 2.8 |
| Tegoamin ZE-1 | 0.5 | 0.35 | 0.35 | 0.5 | 0.5 |
| Kosmos EF | 0.5 | 0.5 | 0.5 | 0.9 | 0.9 |
| Niax L 595 | 0.5 | 0.5 | 0.5 | 0.7 | 0.7 |
| TCPP | 0 | 5 | 5 | 0 | 0 |
| EDAB-DOPO | 0 | 0 | 0 | 5 | 5 |
| Density (Kg/M3) | 42.5 | 47.2 | 25.4? | 46.0 | 30.0 |
| CLD 40% (Kpa) DIN EN ISO 3381/1 | 3.1 | 3.5 | 3.0 | 2.5 | 2.6 |
| Airflow (lt/m2/s) DIN EN ISO 9237 | 7.9 | 57 | 500 | 161 | 414 |
| BKZ Class (Vertical) | X burns | 5 | X burns | 5 | 5 |
| UL 94 HB test rating (Horizontal) | X burns | HF2 | HF2 | HF2 | HF2 |

Discussion of the Results of Table 7:

Columns 1 to 3 are not examples of the invention. 4 and 5 demonstrate the effect of EDAB-DOPO. One can see that at same water level (1.6 pphp) EDAB-DOPO has a positive effect on flammability (Comparison Columns 4 and 1) and works at least as well than TCPP (columns 4 and 2). What is unexpected is that despite having isocyanate reactive groups (see structure in example 12 page 16) the resulting foam is more open airflow 161 versus 57 (l/m2/s) and needs more Kosmos EF indicated better processabilty (flexibility in production). At lower density (2.8 pphp water) EDAB-DOPO works better at least in vertical tests (Comparison columns 3 and 5).

A proof of the efficiency of TEPA-PDOPO in polyether is given in table 8.

Work was done in handmixes.

|  | 1 | 2 | 3 | 4 |
|---|---|---|---|---|
| OH terminated prepolymer OH 30, all PO | 100 | 100 | 100 | 100 |
| TDI 80/20 | 31.9 | 31.9 | 31.9 | 31.9 |
| Water | 2.8 | 2.8 | 2.8 | 2.8 |
| Tegoamin ZE-1 | 0.35 | 0.35 | 0.35 | 0.35 |
| Kosmos EF | 0.7 | 0.7 | 0.7 | 0.7 |
| Tegostab B 8232 | 0.8 | 0.8 | 0.8 | 0.8 |
| Exolit OP 560 | 0 | 10 | 0 | 0 |
| TEPA-PDOPO | 0 | 0 | 5 | 10 |
| Density (Kg/M3) | 38.5 | Shrinks | 40.6 | 42 |
| CLD 40% (Kpa) DIN EN ISO 3381/1 | 7.3 | No Foam | 5.82 | 5.80 |
| BKZ Class (Vertical) | X burns |  | X Burns | 5 |
| UL 94 HB test rating (Horizontal) | X burns |  | HF2 | HF1 |

OH terminated prepolymers are described in patent WO 2005/108455 (Fritz Nauer Ag)

Exolit OP 560 is a leading reactive halogen free flame retardant from Clariant

One can clearly see the improvement of flammability versus the blank. Exolit OP 560 cannot be processed anymore at 10 pphp as it closes so much the foam that cells shrink. The addition of more TEPA-PDOPO improves flammability behavior in both horizontal and vertical tests.

Evaluation of EDAB-DOPO and TEPA-PDOPO in Rigid Formulations

Flame Retardancy of Polyurethane and Polyisocyanurate Foams:

The leading method for flame retarding rigid foam at present is to use additives, although reactive diols are occasionally employed where there is some special requirement. The well-established additives are still TCEP, i.e. tris(2-chloroethyl) phosphate, and TCPP, i.e. tris(1-chloro-2-propyl)phosphate. The recent need for higher percentages of these additives was due to the use of HFCs or of hydrocarbon blowing agents in place of the phased out ozone-depleting chlorofluorocarbons.

The use of pentanes (cyclopentane, isopentane, n-pentane or mixture) for blowing of the foams in place of chlorofluorocarbon blowing, imposes a need for more flame retardants to counteract the flammability of the blowing agent.

Further it is well known that by raising the isocyanate index to get more isocyanurate structure, a lower level of flame retardant can be used to meet a standard. The higher the isocyanurate content, the greater the char yield on fire exposure and thus the more flame resistant, but also the more brittle (friable).

Non-ozone-depleting blowing agents containing fluorine, i.e. HFCs, can allow for less flame retardant, especially in combination with a high isocyanurate content.

Although the chloroalkyl phosphates continue to dominate, there is an interest especially in Europe in non-halogenated flame retardants.

However, in case of fire, halogenated fire retarded polyurethanes evolve more toxic combustion products than the untreated polymer.

These are the reasons why current research focuses on the development of halogen-free and non-toxic fire retardants.

Classification and Testing of the Fire Performance of Building Materials and Components—the DIN 4102 Standard:

Compliance/conformity with building inspection regulations can be substanciated with the aid of the standards generally recognized as standard building practice.

The DIN 4102 Standard—Fire Performance of Building Materials and Components—defines in tangible terms the terminology of fire protection (combustible and non-combustible) employed in the rules and regulations covering building inspection and fire protection.

According to DIN 4102—Part 1 building materials can be classified in class A (non-combustible) or class B (combustible).

Owing to their organic structures, plastics usually achieve only class B.

Acc. to DIN 4102-1 combustible building materials can be classified in following categories:

1. B 1=Low flammability (Brandschacht test)
2. B 2=Moderately flammable (Small Burner test)
3. B 3=Highly flammable The test methods and requirements for combustible and (non-combustible building) materials are described in different sections of DIN 4102-1.

Class B2 Building Materials:

Building materials achieve class B2 if they satisfy the test requirements given in the following table

| Specimens | 4. Edge application of flame; five specimens 90 mm × 190 mm × original thickness (max. 80 mm), reference mark 150 mm from lower edge |
| | 5. Surface application of flame: five specimens 90 mm × 230 mm × original thickness (max. 80 mm), reference marks 40 mm and 150 mm from lower edge |
| Specimen position | 6. Vertical |
| Ignition source | 7. Small flame burner, inclined at 45°, flame height 20 mm |
| Flame application | 8. 15 s |
| Test duration | 9. 20 s |
| Continued: | 10. |
| Conclusions | 11. Passed if the tip of the flame does not reach the reference marks within 20 s on any sample for: |
| | 12. If the filter paper under the sample ignites within 20 s after flaming, the material is judged to burn with flaming droplets. |

Small Burner Test Equipment:

The Small Burner test equipment employed within this patent is in accordance to the requirements for the tests of the building materials class B2 specified in DIN 4102-1.

All flame tests done within this report are based on edge application of the impinging flame.

Dispersing EDAB-DOPO/TEPA-PDOPO:

EDAB-DOPO resp. TEPA-PDOPO were dispersed into the polyol-components by means of high speed dispersion in order to incorporate extremely fine solid particles into the fluids, to produce colloidal suspensions. The preparations of the dispersions were carried out (prior to adding the respective blowing agents) at high peripheral velocities (formation of the doughnut-effect).

Equipment Used:

IKA "Eurostar Power Control—Visc 6000" (speed range up to 6000 rpm) with dissolver disc IKA "R 1402 Dissolver".

For the dispersing of EDAB-DOPO resp. TEPA-PDOPO into the polyol component, high intensity ultrasonication could be an improved alternative to using a rotor-stator mixer.

Ultrasonic preparation of solids into liquids has been proven to be more effective than other high-shear mixing methods (14). At appropriate energy levels ultrasonication could achieve reduction in particle size of one to two magnitudes.

Efficiency of highly dispersed flame retardants of submicrometer particle size (0.1- to 1.0 μm is discussed by Levchik (15)

Description of the Chemicals

| | |
|---|---|
| Petol PM 500 - 3F | Mannich - Polyether Polyol; OH-No. 480-520; f = 3.0-3.5; visc. 5000-11000 mPa s (25° C.) |
| Rokopol RF- 551 | Sorbitol-based Rigid Polyether Polyol; OH-No. 400-440; f = ca. 4.5; visc. 3000-5000 mPa s (25° C.) |
| Stepanpol PS-2352 | Aromatic Rigid Polyester Polyol (o-Phthalate-Diethyleneglycol based); OH-No. ca. 240; f = 2.0; visc. 3000 mPa s (25° C.) |
| Dabco DC 193 | Rigid Foam Silicone Surfactant |
| Dabco TMR-2 | Amine based, blocked trimerisation catalyst |
| Polycat 9 | Tris (dimethyl aminopropyl)amine; blowing catalyst 4 |
| Polycat 41 | Triazine derivative; trimerisation catalyst |
| Polycat 77 | Pentamethyl dipropylene triamine; blow/gel catalyst |
| Kitane 20 AS | Emulsifier/compatiliser for pentane blown foams |
| Solkane 365mfc/227ea | HFCs; 365mfc:227ea = 93:7; Bp. 30° C.; classified as non flammable |
| Pentane | n-Pentane; Bp. 36° C. |
| Desmodur 44 V 20 L | PMDI; f = ca. 2.7; visc. 160-240 mPa s (25° C.) |
| Desmodur 44 V 40 L | PMDI; f = ca. 2.9; visc. 350-450 mPa s (25° C.) |

Test Results:

The B2-burner tests were carried out approx. one week after foaming.

1. Sandwich Panel (SP):

All prepared sandwich panel specimens were of high macroscopic quality, i.e. very fine and regular cell structure. No shrink within shelf time of approx. four weeks after preparation.

No flame droplings occurred on fire exposure.

Formulations for discontinous Panel production (blowing agent HCF 365 mfc/227 ea) with TCPP as flame retardant were set up as bench mark.

A formulation containing 3.0 pbw of EDAB-DOPO blown with 365 mfc/227 ea (compare formulation SP-12 with 365 mfc/227 ea vs. formulation SP-10 with TCPP gave similar results reg. flame height and flame extinguishing demonstrating the efficiency of EDAB-DOPO in SP formulations.

Sandwich Panel (SP)—Solkane 365 mfc/227 ea

| | SP-10 | SP-12 |
|---|---|---|
| Rokopol RF-551 | 10.0 | 10.0 |
| Stepanpol PS 2352 | 40.0 | 40.0 |
| TCPP | 15.0 | 0.0 |
| Dabco-TMR-2 | 2.5 | 2.5 |
| Polycat 77 | 0.45 | 0.45 |
| Polycat 41 | 0.15 | 0.15 |
| Dabco DC 193 | 2.0 | 2.0 |
| Kitane 20 AS | 0.0 | 0.0 |
| Water | 0.50 | 0.5 |
| EDAB - DOPO | 0 | 3.0 |
| Solkane 365 mfc/227 ea | 10 | 10.0 |
| Index | 250 | 250 |
| Desmodur 44 V 40 L (PMDI; f = ca. 2.9) | 101 | 101.0 |
| Foam structure (very fine and regular = very good) | v.g. | v.g. |
| Flame height (cm) | 13-14 | 16-17 |
| Flame extinguishes after 15 s impinging plus x sec. | x = 0-1 | x = 0-1 |
| Density (kg/cm$^3$) | 39.2 | 41.2 |

HFC 365 mfc/227 ea was used for sandwich panels in case of discontinuous manufacturing; while pentane is standard for continuous production.

Further work indicate that EDAB-DOPO resp. TEPA-PDOPO could need the synergism of an efficient intumescent char former like expandable graphite in combination with an efficient carbonaceous char former like pentaerythritol to be efficient in pentane formulations.

From an individual point of conception the application of EDAB-DOPO resp. TEPA-PDOPO in combination with effective intumescent and cabonaceous char formers, like expandable graphite and pentaerythritol, have a pronounced effect on smoke reduction from sandwich panel burning (compared to the application of TCPP). Quantitative results conc. smoke density are to be obtained from Cone Caborimetry (CC).

2. Spray Foam (SPF):

All prepared spray foam specimens were of high macroscopic quality, i.e. very fine and regular cell structure. No shrink within shelf time of approx. four weeks after preparation.

No flame droplings occurred on fire exposure.

Formulations of Spray Foam (blowing agent HFC 365 mfc/227 ea) with TCPP as flame retardant were set up as bench mark.

Spray Foam (SPF)—Solkane 365 mfc/227 ea

| Product | SPF-11 | SPF-17 | SPF-18 | SPF-19 | SPF21 |
|---|---|---|---|---|---|
| Petol PM 500-3F | 43.0 | 43.0 | 43.0 | 43.0 | 43.0 |
| Stepanpol PS 2352 | 31.0 | 31.0 | 31.0 | 31.0 | 31.0 |
| TCPP | 10.0 | 0 | 0 | 0 | 0 |
| Dabco DC 193 | 3.0 | 3.0 | 3.0 | 3.0 | 3.0 |
| Dabco TMR 2 | 2.00 | 2.0 | 2.0 | 2.0 | 2.0 |
| Polycat 9 | 0.85 | 0.85 | 0.85 | 0.85 | 0.85 |
| Polycat 41 | 0.15 | 0.15 | 0.15 | 0.15 | 0.15 |
| Water | 1.0 | 1.0 | 1.0 | 1.0 | 1.0 |
| EDAB -DOPO | 0 | 3.0 | 0 | 6.0 | 0 |
| TEPA-PDOPO | 0 | 0 | 3.0 | 0 | 0 |
| Solkane 365 mfc/227 ea | 10.0 | 10.0 | 10.0 | 10.0 | 10.0 |
| Desmodur 44 V 20 L (PMDI; f = ca. 2.7) | 0 | 0 | 0 | 0 | 0 |
| Desmodur 44 V 40 L (PMDI; f = ca. 2.9) | 150 | 150 | 150 | 150 | 150 |
| Index | 175 | 175 | 175 | 175 | 175 |
| Foam structure very fine and regular = very good | v.g. | v.g. | v.g. | v.g. | v.g. |
| Flame height (cm) | 12.5-13.5 | 14.5-15 | 15-16 | 14 | >20 |
| Flame extinguishes after 15 s impinging plus x sec. | x = 1 | x = 3 | x = 4 | x = 1 | x = 9 |
| Density (kg/m$^3$) | 40 | 43.1 | 41.7 | 41.4 | 43.7 |

Reference formulation is SPF-11 (TCPP; Index 175). It shows outstanding results.

Flame test results of SPF 11 are very good because of high TCPP content and/or higher PMDI-index, which results in a higher PIR content in the foam (and thus higher char formation on fire exposure).

Acceptable results with EDAB-DOPO resp. TEPA-PDOPO were achieved with formulations SPF-17 to SPF-19 (3.0 resp. 6.0 parts of EDAB-DOPO resp. TEPA-PDOPO. Compare results against the "blind" test SPF-21.

Remarkable and unexpected is the fact that doubling the amount of EDAB-DOPO resp. TEPA-PDOPO has no significant effect on flame height and extinguishing of the flame.

[1] Lu, S.-H., Hamerton, I. *Progress in Polymer Science* 2002 27(8), 1661-1712.

[2] a) Lu, L. et al U.S. Pat. Appl. Publ. 2011, 20110034717; b) Doering, M. et al. *Ger. Offen.* 2010 102009035301; c) Buysch, H.-J. et al *Ger. Offen.* 1996, 19505352; d) Saito T. 1972 U.S. Pat. No. 3,702,878

[3] a) Shieh, J.-Y.; Wang, C.-S. *Polymer* 2001, 42, 7617; b) Dittric, U.; Just, B.; Doering, M.; Ciesielski, M. US Patent Application Publication 2005, US 2005/0020739 A1; c) Wang, X.-j.; Wang, R.-m.; Yang, J.-H. *Reguxing Shuzhi* 2009, 24, 27; d) Just, B.; Imeri, S.; Keller, H.; Storzer, U. *Eur. Pat. Appl.* 2009, EP 2090618 A2 20090819; e) Tobisawa, A. *Jpn. Kokai Tokkyo Koho* 2002, JP 2002161197 A 20020604; f) Just, B.; Dittrich, U.; Keller, H.; Döring, M.; Storzer, U.; Ciesilski, M. 2010, US 2010280215 A1.

[4] a) Koenig, A.; Kroke, E. *From Polymers for Advanced Technologies* 2011, 22, 5; b) Zhao, X. *Huaxue Yanjiu Yu Yingyong* 2000, 12, 648.

[5] Schaefer, A., Seibold, S., Lohstroh, W., Walter, O., Döring, M. *Journal of Applied Polymer Science* 2007, 105(2), 685-696.

[6] a) Beletskaya, I. P.; Neganova, E. G.; Veits, Y. A. *Russian Journal of Organic Chemistry*, 2004, 40, 1782; b) Sponton, M.; Lligadas, G.; Ronda, J. C.; Galia', M.; Cadiz, M. *Polymer Degradation and Stability* 2009, 94, 1693.

[7] a) Lindner, B.; Kammerer, F.; Kohl, C. PCT Int. Appl. 2011, WO 2011000457A120110110 b) Saito, T.; Kim, S. H.; Kim, J. S.; Park, J. H. *Jpn. Kokai Tokkyo Koho* 2007, JP 2007091606A20070412; c) Yun, K. K.; Kim, Y. C.; Choi, T. K.; Park, I. S. *Repub. Korea* 1999, KR 199102 B1 1999061; d) Wang, C. S.; Hsieh, C. Y.; Lin, C. Y. *Jpn. Kokai Tokkyo Koho* 2003, JP 2003105058 A 2003040; e) Feng, L.; Tang, A.; Xu, Z.; Li, S. *Faming Zhuanli Shenqing Gongkai Shuomingshu* 2007 CN 100999145 A 20070718; f) Salto, T.; Kim, S. H.; Kim, J. S.; Park, J. H Jpn. Kokai Tokkyo Koho 2006, JP 2006328100 A 20061207. g) Kanno, T., Sugata, Y., Yanase, H., Shigehara, K., PCT Int. Appl. 2006 WO 2006126393 A1 20061130. h) Kerenyi, A.; Balassa, A.; Kortvelyesi, T.; Ludanyi, K.; Keglevich, G. *Transition Metal Chemistry* 2008, 33, 459; i) Keglevich, G., Szelke, H., Kerenyi, A., Kudar, V., Hanusz, M., Simon, K., Imre, T., Ludanyi, K. *Tetrahedron Asymmetry* 2005 16(24), 4015-4021; j) Ábrányi-Balogh, P.; Keglevich, G. *Synth. Comm.* 2011, 41, 1421-1426; k) Ujj, V.; Czugler, M.; Schindler, J.; Fogassy, E.; Keglevich, G. *Magyar Kemial Folyoirat, Kemiai Kozlemenyek* 2010, 116, 31.

[8] b) Jung, G. C.; Hyeon, N.; Park, I. G.; Yoo, J. H.; Hyun, A. R.; Jung, Y. H. Repub. Korean Kongkae Taeho Kongbo 2008, KR 2008091036 A 20081009; a) Hinohara, A.; Hayashi, T.; Nogi, S.; Ikemoto, K.; Saito, T. Jpn. Kokai Tokkyo Koho 2009, JP 2009266663 A 20091112; c) Uchida, O., Sato, K. *Jpn. Kokai Tokkyo Koho* 1998 JP 10203028 A 19980804.

[9] a) Zich, T.; Artner, J.; Mehofer B.; Döring, M.; Ciesielski, M.; Zwick, G.; Rakotomalala, M. 2011, AT 508468A1; b) Rakotomalala, M; Wagner, S.; Zevaco, T.; Döring, M. *Heterocycles* 2011, 83, 743-753

[10] a) Gaan, S., Rupper, P., Salimova, V. *POLYMER DEGRADATION AND STABILITY* 2009 94(7), 1125-1134; b) Deo, H. T.; Patel, N. K.; Patel, B. K. *J. of Engineered Fibers and Fabrics* 2008, 3(4), 23-38. c) Leu, T.-S.; Wang, C.-S. *J. of Applied Polymer Science* 2004, 92(1), 410-417. d) Nguyen, C.; Kim, J. *Polymer Degradation and Stability* 2008, 93, 1037-1043. e) Lewin, M. *J. of Fire Sciences* 1999, 17(1), 3-19.

[11] Toshiyuki, K.; Yoshinobu, S.; Hironori, Y.; Kiyotaka, S 2008, EP 1889878 A1

[12] Wang, L., Wu, X., Wu, C., Yu, J., Wang, G., Jiang, P. *Journal of Applied Polymer Science* 2011, 121(1), 68-77.

[13] a) Risk Assessment Report on Tris(2-Chlor-propyl) Phosphate (TCPP), *Scientific Committee on Health and Environmental Risks, Environmental Part* 2007, EINECS No. 237-158-7. b) Gupta, R. *Toxicology of Organophosphate* and *Carbamate compounds* 2006, ISBN: 978-0-12-088523-7, Elsevier Inc. Burlington, Mass.

[14] Stein, H. N.: The Preparation of Dispersions in Liquids, New York 1995, p. 62 f.

[15] Levchik, S. V.; Introduction to Flame Retardancy and Polymer Flammability, in: Morgan, A. B. and Wilkie, C. A. (Eds.): Flame Retardant Polymer Nanocomposites, Hoboken/NJ 2007, p. 20 ff. (ibid. further references)

The invention claimed is:

1. A phosphonamidate compound selected from the group consisting of:

AA-DOPO: 6-(allylamino)-6H-dibenzo [c,e] [1,2] oxaphosphinine 6-oxide;

PB-DOPO: 6,6'-(piperazine-1,4-diyl)bis(6H-dibenzo [c,e][1,2] oxaphosphinine 6-oxide);

PDAB-DOPO: 6,6'-(1,4-phenylenebis(azanediyl))bis (6H-dibenzo [c,e][1,2] oxaphosphinine 6-oxide);

TMSPA-DOPO: 6-((3-(trimethoxysilyl)propyl)amino)-6H-dibenzo[c,e][1,2]oxaphosphinine 6-oxide;

a compound according to Formula (I)

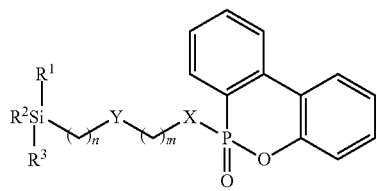

(I)

$R^1$ = H, alkyl (C1-8), alkoxy (C1-8), amine (C1-8), OH, SR (R = H, alkyl), O-metal
$R^2$ = H, alkyl (C1-8), alkoxy (C1-8), amine (C1-8), OH, SR (R = H, alkyl), O-metal
$R^3$ = H, alkyl (C1-8), alkoxy (C1-8), amine (C1-8), OH, SR (R = H, alkyl), O-metal
Y = NH, N-DOPO moiety, O, S
X = NH, NR (R = alkyl)
n = 1-8
m = 1-8

DOPO moiety = 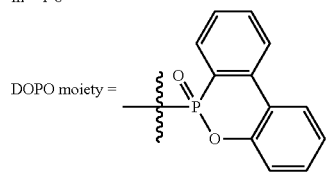

a compound according to Formula (II)

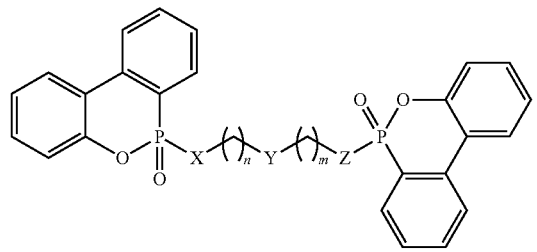

(II)

X = NR (R = H, alkyl),
Y = N-DOPO moiety, CH$_2$
Z = NR (R = H, alkyl),
m = 0-8
n = 0-8

DOPO moiety = 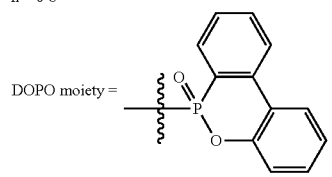

a compound according to formula (III)

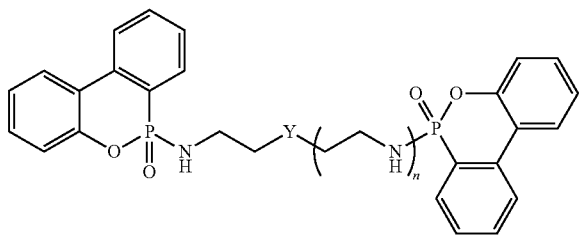

(III)

Y = NR [R = H, alkyl, DOPO-moiety, PO(OR)$_2$ (R = alkyl or aryl), PO(OR$^1$)R$^2$ (R$^1$ = alkyl or aryl, R$^2$ = alkyl or aryl), COR (R = 0-alkyl, NH$_2$, NH-alkyl, N-(alkyl)$_2$, alkyl or aryl), carbonyl, SiR$_3$ (R = alkyl, alkoxy)], n = 0-100 and mixtures thereof, a compound according to formula (IV)

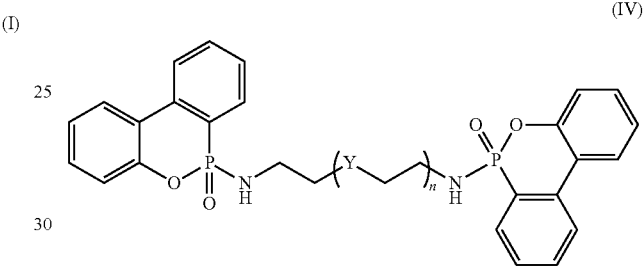

(IV)

Y = NR [R = H, alkyl, DOPO-moiety, PO(OR)$_2$ (R = alkyl or aryl), PO(OR$^1$)R$^2$ (R$^1$ = alkyl or aryl, R$^2$ = alkyl or aryl), COR (R = 0-alkyl, NH$_2$, NH-alkyl, N-(alkyl)$_2$, alkyl or aryl), carbonyl, SiR$_3$ (R = alkyl, alkoxy)], n = 0-100 and mixtures thereof, wherein AA-DOPO, PB-DOPO, PDAB-DOPO, and TMSPA-DOPO, are defined as follows:

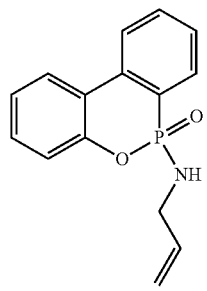

6-(allylamino)-6H-dibenzo[c,e][1,2]oxaphosphinine 6-oxide (AA-DOPO)

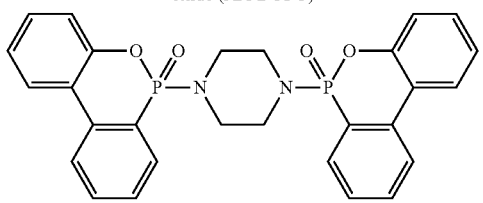

6,6'-(piperazine-1,4-diyl)bis(6H-dibenzo[c,e][1,2] oxaphosphinine 6-oxide) (PB-DOPO)

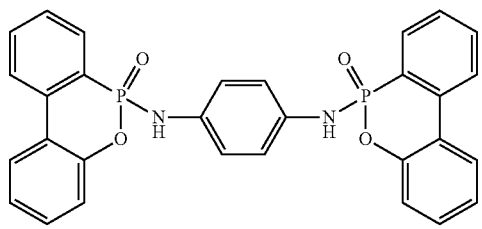

6,6'-(1,4-phenylenebis(azanediyl))bis(6H-dibenzo[c,e][1,2]oxaphosphinine 6-oxide) (PDAB-DOPO)

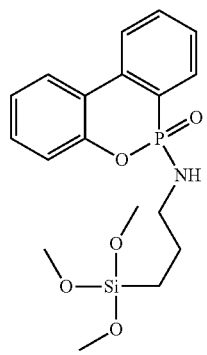

6-((3-(trimethoxysilyl)propyl)amino)-6H-dibenzo[c,e][1,2]oxaphosphinine 6-oxide (TMSPA-DOPO).

2. A phosphonamidate compound according to claim 1, wherein the compound is not AA-DOPO or PDAB-DOPO.

3. A phosphonamidate compound according to claim 1, wherein the compound is according to formula (III) and is EDAB-DOPO defined as:

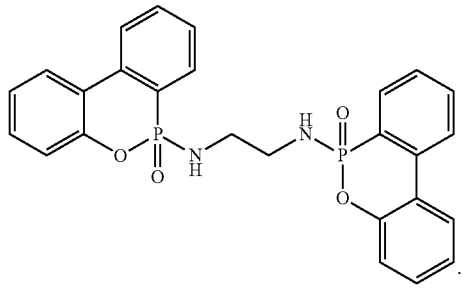

6,6'-(ethane-1,2-diylbis(azanediyl))bis(6H-dibenzo [c.e][1,2]oxaphosphinine 6-oxide) (EDAB-DOPO).

4. A method of improving flame resistance of a polymeric material, comprising the step of adding a first amount of a phosphonamidate as defined in claim 1, or of a mixture thereof, as a flame retardant substance to a second amount of said polymeric material.

5. The method according to claim 4, wherein said flame retardant substance is selected from the group consisting of:
AA-DOPO,
PB-DOPO,
EDAB-DOPO

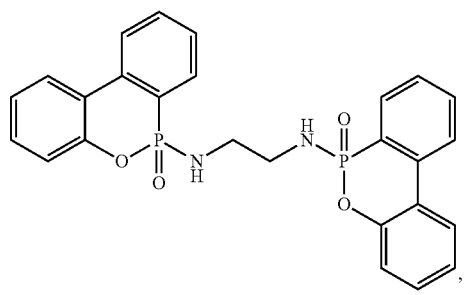

6,6'-(ethane-1,2-diylbis(azanediyl))bis(6H-dibenzo[c,e][1,2]oxaphosphinine 6-oxide) (EDAB-DOPO)

DEA-DDOPO, which is a compound according to formula (II),

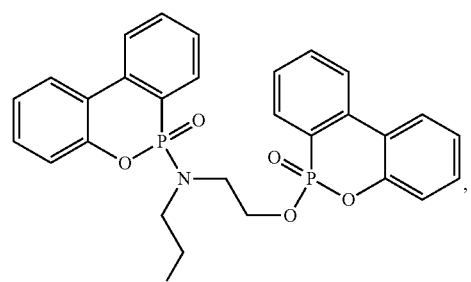

6-((2-hydroxyethyl)(2-((6-oxido-6H-dibenzo[c,e][1,2]oxaphosphinin-6-yl)oxy)ethyl)amino)-6H-dibenzo[c,e][1,2]oxaphosphinine 6-oxide (DEA-DDOPO)

and mixtures thereof.

6. The method according to claim 4, wherein said flame retardant substance is selected from the group consisting of:
AA-DOPO,
EDAB-DOPO

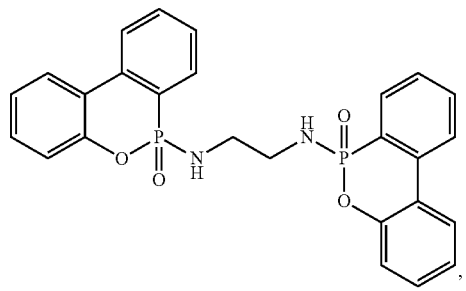

6,6'-(ethane-1,2-diylbis(azanediyl))bis(6H-dibenzo[c,e][1,2]oxaphosphinine 6-oxide) (EDAB-DOPO)

and
  a mixture comprising DEA-TDOPO, which is a compound according to formula (II), and DEA-DDOPO

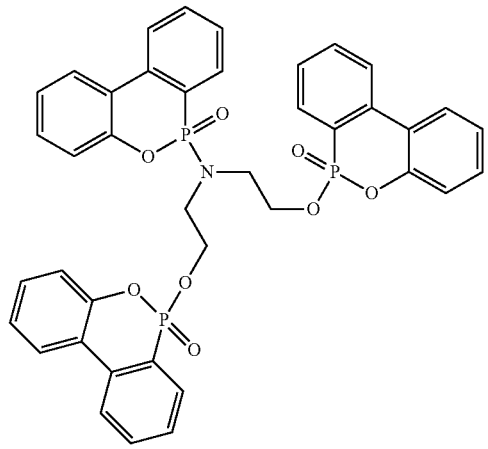

6,6'-((((6-oxido-6H-dibenzo[c,e][1,2]oxaphosphinin-6yl)azanediyl)bis
(ethane-2,1-diyl)bis)(oxy))
bis(6Hdibenzo[c,e][1,2]oxaphosphinine 6-oxide)
(DEA-TDOPO)

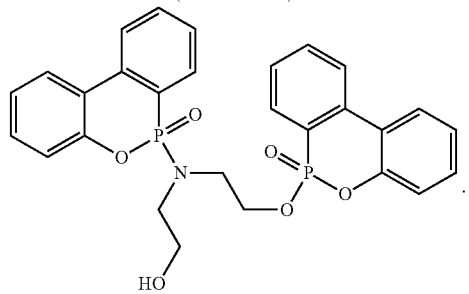

6-((hydroxyethyl)(2-((6-oxido-6H-dibenzo[c,e][1,2]oxaphosphinin-6-
yl)oxy)ethyl)amino)-6H-dibenzo[c,e][1,2]oxaphosphinine 6-oxide
(DEA-DDOPO)

7. The method according to claim 4, wherein said flame retardant substance comprises DEA-DDOPO

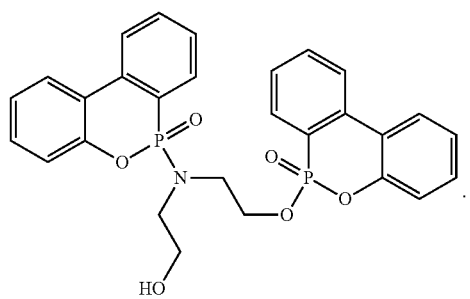

6-((2-hydroxyethyl)(2-((6-oxido-6H-dibenzo[c,e][1,2]oxaphosphinin-6-
yl)oxy)ethyl)amino)-6H-dibenzo[c,e][1,2]oxaphosphinine 6-oxide
(DEA-DDOPO)

8. The method according to claim 4, wherein said flame retardant substance is admixed to a polyurethane foam formulation or added to a polyurethane foam as a post treatment.

9. The method according to claim 4, wherein said flame retardant substance is admixed to a flexible polyurethane foam formulation or added to a flexible polyurethane foam as a post treatment, wherein the flexible polyurethane foam or foam formulation is a polyether or polyester flexible polyurethane foam, or a combination thereof.

10. A polymeric material with improved flame resistance, comprising a flexible polyurethane foam containing an amount of 1% to 30% by weight per 100 parts of polyol of a flame retardant additive selected from a phosphonamidate compound of claim 1.

11. A polymeric material with improved flame resistance, comprising a rigid polyurethane foam containing an amount of 1% to 30% by
  weight per 100 parts of polyol of a flame retardant additive selected from a phosphonamidate compound of claim 1,
and optionally also comprising a synergist.

12. A method of making a phosphonamidate according to claim 1, wherein this method comprises the steps of:
  (a) dissolving DOPO and an amine in a solvent to form a mixture,
  (b) optionally cooling the mixture to below about 10° C.,
  (c) adding tetrachloromethane to the mixture at a rate such that (i) the reaction temperature does not exceed about 30° C., or if the mixture was cooled, (ii) such that the reaction temperature does not exceed about 20° C.,
  (d) allowing the mixture to return to about 25° C., and stirring.

13. A method of making a phosphonamidate according to claim 1, wherein this method comprises the steps of:
  (a) dissolving DOPO and an amine in a solvent to form a mixture,
  (b) optionally cooling the mixture to below about 10° C.,
  (c) adding trichloroisocyanuric acid to the mixture at a rate such that (i) the reaction temperature does not exceed about 30° C., or if the mixture was cooled, (ii) such that the reaction temperature does not exceed about 20° C.,
  (d) allowing the mixture to return to about 25° C., and stirring.

14. A method of improving flame resistance of a substance, the method comprising adding a phosphonamidate compound according to claim 1 to the substance.

15. A method of improving flame resistance of a polyurethane foam, the method comprising adding a phosphonamidate compound according to claim 1 to the polyurethane foam.

16. A phosphonamidate compound according to claim 1, wherein the compound is selected from the group consisting of:
  AA-DOPO: 6-(allylamino)-6H-dibenzo [c,e] [1,2] oxaphosphinine 6-oxide;
  PB-DOPO: 6,6'-(piperazine-1,4-diyl)bis(6H-dibenzo [c,e][1,2] oxaphosphinine 6-oxide); and
  PDAB-DOPO: 6,6'-(1,4-phenylenebis(azanediyl))bis (6H-dibenzo [c,e] [1,2] oxaphosphinine 6-oxide).

17. A phosphonamidate compound according to claim 1, wherein the compound is according to formula (I) and is selected from the group consisting of:
  TESPA-DOPO: 6-((3-(triethoxysilyl)propyl)amino)-6H-dibenzo[c,e] [1,2]oxaphosphinine 6-oxide

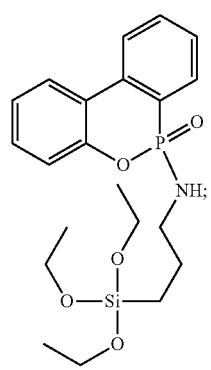 [SMILES: CCO[Si](CCCNP1(=O)Oc2ccccc2-c2ccccc21)(OCC)OCC]

and

TMSPA-DOPO: 6-((3-(trimethoxysilyl)propyl)amino)-6H-dibenzo[c,e] [1,2]oxaphosphinine 6-oxide.

18. A phosphonamidate compound according to claim 1, wherein the compound is according to formula (II) and is selected from the group consisting of:

EAB-DOPO: 6-(2-((6-oxido-6H-dibenzo [c,e] [1,2]oxaphosphinin-6-yl)amino)ethoxy)-6H-dibenzo[c,e] [1,2]oxaphosphinine 6-oxide

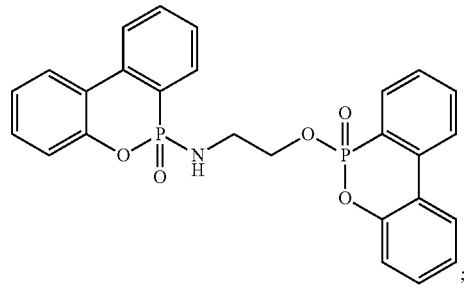 [SMILES: O=P1(NCCOP2(=O)Oc3ccccc3-c3ccccc32)Oc2ccccc2-c2ccccc21]

DEA-DDOPO: 6-((2-hydroxyethyl)(2-((6-oxido-6H-dibenzo[c,e] [1,2]oxaphosphinin-6-yl)oxy)ethyl)amino)-6H-dibenzo [c,e] [1,2]oxaphosphinine 6-oxide

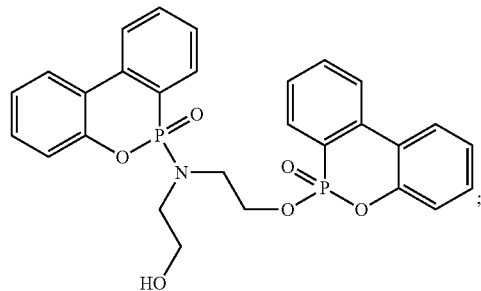 [SMILES: O=P1(OCCN(CCO)P2(=O)Oc3ccccc3-c3ccccc32)Oc2ccccc2-c2ccccc21]

and

DEA-TDOPO: 6,6'-(((((6-oxido-6H-dibenzo[c,e] [1,2]oxaphosphinin-6-yl)azanediyl)bis(ethane-2,1-diyl))bis(oxy))bis(6Hdibenzo [c,e] [1,2]oxaphosphinine 6-oxide)

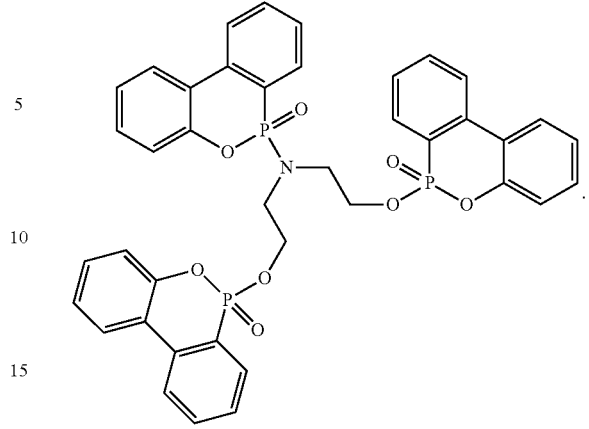

19. A phosphonamidate compound according to claim 1, wherein the compound is according to formula (III) and is selected from the group consisting of:

EDAB-DOPO: 6,6'-(ethane-1,2-diylbis(azanediyl))bis(6H-dibenzo[c,e] [1,2]oxaphosphinine 6-oxide)

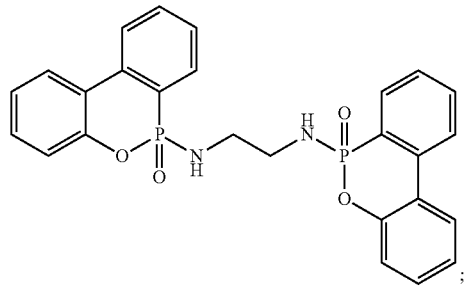 [SMILES: O=P1(NCCNP2(=O)Oc3ccccc3-c3ccccc32)Oc2ccccc2-c2ccccc21]

and

TDETA-DOPO: 6-((3-((6-oxido-6H-dibenzo[c,e] [1,2]oxaphosphinin-6-yl)(2-((6-oxido-6Hdibenzo[c,e] [1,2]oxaphosphinin-6-yl)amino)ethyl)amino)propyl)amino)-6H-dibenzo [c,e][1,2]oxaphosphinine 6-oxide

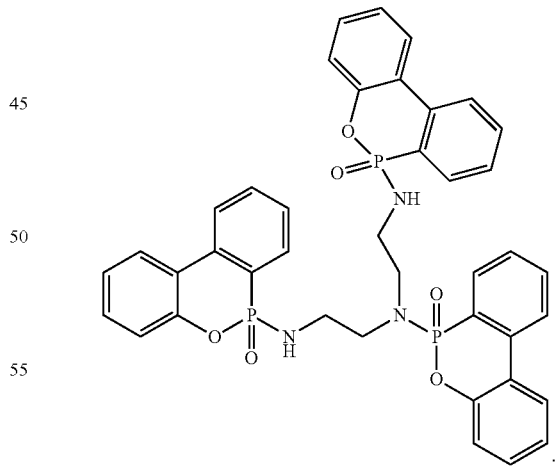

20. A phosphonamidate compound according to claim 1, wherein the compound is according to formula (IV) and is comprises:

TEPA-PDOPO: 6,6'-(((((6-oxido-6H-dibenzo[c,e] [1,2]oxaphosphinin-6-yl)azanediyl)bis(ethane-2,1-diyl))bis((2-((6-oxido-6H-dibenzo[c,e] [1,2]oxaphosphinin-6-yl)amino)ethyl)azanediyl))bis(6Hdibenzo[c,e] [1,2]oxaphosphinine 6-oxide)

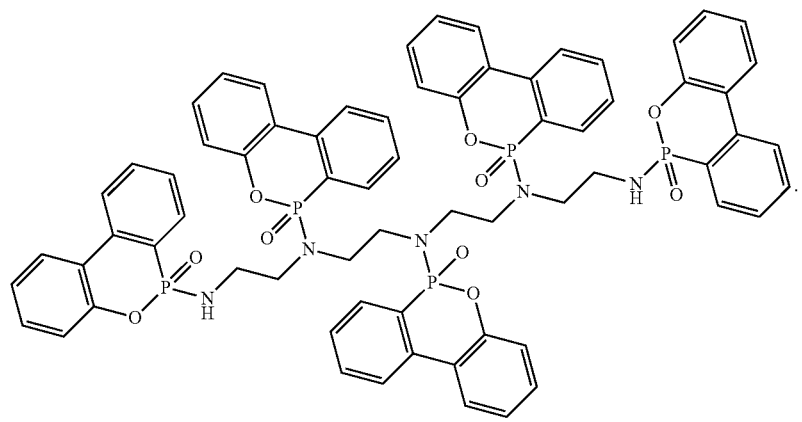
* * * * *